(12) United States Patent
Habte et al.

(10) Patent No.: US 10,194,821 B2
(45) Date of Patent: *Feb. 5, 2019

(54) MEDICAL DEVICE HAVING AUTOMATED ECG FEATURE EXTRACTION

(71) Applicant: KHALIFA UNIVERSITY OF SCIENCE AND TECHNOLOGY, Abu Dhabi (AE)

(72) Inventors: Temesghen Tekeste Habte, Asmara (ER); Nourhan Yahya Bayasi, Ajman (AE); Hani Hasan Mustafa Saleh, Abu Dhabi (AE); Ahsan Habib Khandoker, Abu Dhabi (AE); Baker Mohammad, Abu Dhabi (AE); Mahmoud Al-Qutayri, Abu Dhabi (AE); Mohammed Ismail Elnaggar, Abu Dhabi (AE)

(73) Assignee: Khalifa University of Science and Technology, Abu Dhabi (UA)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,554

(22) Filed: Oct. 29, 2015

(65) Prior Publication Data

US 2016/0120431 A1 May 5, 2016

Related U.S. Application Data

(60) Provisional application No. 62/069,975, filed on Oct. 29, 2014, provisional application No. 62/074,409, filed on Nov. 3, 2014.

(51) Int. Cl.
*A61B 5/0456* (2006.01)
*A61B 5/0468* (2006.01)
(Continued)

(52) U.S. Cl.
CPC .......... *A61B 5/0468* (2013.01); *A61B 5/0245* (2013.01); *A61B 5/02405* (2013.01);
(Continued)

(58) Field of Classification Search
CPC . A61B 5/0245; A61B 5/04012; A61B 5/0402; A61B 5/0428; A61B 5/0432;
(Continued)

(56) References Cited

U.S. PATENT DOCUMENTS 7,610,086 B1 10/2009 Ke et al.
2005/0004481 A1* 1/2005 Xue ..................... A61B 5/0452
600/509

(Continued)

OTHER PUBLICATIONS

C. Li, C. Zheng and C. Tai. "Detection of ecg characteristic points using wavelet transforms". Biomedical Engineering, IEEE Transactions on, vol. 42, No. 1, pp. 21-28, 1995.*

(Continued)

*Primary Examiner* — Eugene T Wu
(74) *Attorney, Agent, or Firm* — Withrow & Terranova, P.L.L.C.

(57) ABSTRACT

A medical device having automated electrocardiogram (ECG) feature extraction is disclosed. The medical device includes input circuitry configured to receive an ECG signal. Processing circuitry coupled to the input circuitry is configured to identify at least one fiducial point of heartbeat signature of the ECG signal. The processing circuitry is further configured to perform substantially simultaneously both a discrete wavelet transform (DWT) and a curve length transform (CLT) to identify the at least one fiducial point.

11 Claims, 15 Drawing Sheets

(51) Int. Cl.

| | |
|---|---|
| *A61B 5/0428* | (2006.01) |
| *A61B 5/0245* | (2006.01) |
| *A61B 5/00* | (2006.01) |
| *A61B 5/04* | (2006.01) |
| *A61B 5/0464* | (2006.01) |
| *A61B 5/024* | (2006.01) |
| *A61B 5/0402* | (2006.01) |

(52) U.S. Cl.
CPC ........ *A61B 5/0402* (2013.01); *A61B 5/04012* (2013.01); *A61B 5/0428* (2013.01); *A61B 5/0456* (2013.01); *A61B 5/0464* (2013.01); *A61B 5/7264* (2013.01)

(58) Field of Classification Search
CPC . A61B 5/04325; A61B 5/0452; A61B 5/0456; A61B 5/0468; A61B 5/0472; A61B 5/7235; A61B 5/7246; A61B 5/7253; A61B 5/7257; A61B 5/726; A61B 5/7264; A61B 5/7267; A61B 5/7282
See application file for complete search history.

(56) References Cited

U.S. PATENT DOCUMENTS

| | | | |
|---|---|---|---|
| 2007/0203418 A1* | 8/2007 | Starc ................. | A61B 5/04525 600/509 |
| 2007/0276274 A1 | 11/2007 | Kawada et al. | |
| 2010/0217144 A1 | 8/2010 | Brian | |
| 2015/0032990 A1 | 1/2015 | Markovic et al. | |
| 2016/0120430 A1 | 5/2016 | Bayasi et al. | |
| 2017/0265768 A1 | 9/2017 | Bayasi et al. | |

OTHER PUBLICATIONS

J. P. Martinez, R. Almeida, S. Olmos, A. P. Rocha and P. Laguna. "A wavelet-based ecg delineator: evaluation on standard databases". Biomedical Engineering, IEEE Transactions on, vol. 51, No. 4, pp. 570-581, 2004.*

J. Dumont, A. Hernandez and G. Carrault. "Parameter optimization of awavelet-based electrocardiogram delineator with an evolutionary algorithm". Computers in Cardiology, 2005, pp. 707-710, 2005, IEEE.*

T. Tekeste et al., "Adaptive ECG interval extraction," 2015 IEEE International Symposium on Circuits and Systems (ISCAS), Lisbon, 2015, pp. 998-1001.doi: 10.1109/ISCAS.2015.7168804.*

T. Tekeste, H. Saleh, B. Mohammad, A. Khandoker and M. Ismail, "A biomedical SoC architecture for predicting ventricular arrhythmia," 2016 IEEE International Symposium on Circuits and Systems (ISCAS), Montreal, QC, 2016, pp. 2262-2265. doi: 10.1109/ISCAS.2016.7539034.*

N. Bayasi, T. Tekeste, H. Saleh, B. Mohammad and M. Ismail, "A 65-nm low power ECG feature extraction system," 2015 IEEE International Symposium on Circuits and Systems (ISCAS), Lisbon, 2015, pp. 746-749. doi: 10.1109/ISCAS.2015.7168741.*

E. Mazomenos, D. Biswas, A. Acharyya, T. Chen, K. Maharatna, J. Rosengarten, J. Morgan and N. Curzen "A low-complexity ecg feature extraction algorithm for mobile healthcare applications" Biomedical and Health Informatics, IEEE Journal of, vol. 17, No. 2, pp. 459-469, Mar. 2013.*

W. Zong, M. Saeed and T. Heldt. "A qt interval detection algorithm based on ecg curve length transform". Computers in Cardiology, 2006, pp. 377-380, 2006, IEEE.*

W. Zong, G. Moody and D. Jiang. "A robust open-source algorithm to detect onset and duration of qrs complexes". Computers in Cardiology, 2003, pp. 737-740, 2003, IEEE.*

J. Pan and W. J. Tompkins. "A real-time qrs detection algorithm". Biomedical Engineering, IEEE Transactions on, No. 3, pp. 230-236, 1985.*

Author Unknown, "American Heart Association," American Heart Association, Inc., 2016, Accessed: Apr. 19, 2016, 3 pages, Available at: http://www.heart.org/HEARTORG/.

Alonso-Atienza, Felipe et al., "Detection of Life-Threatening Arrhythmias Using Feature Selection and Support Vector Machines," IEEE Transactions on Biomedical Engineering, vol. 61, No. 3, Mar. 2014, pp. 832-840.

Amann, Anton et al., "Detecting Ventricular Fibrillation by Time-Delay Methods," IEEE Transactions on Biomedical Engineering, vol. 54, No. 1, Jan. 2007, pp. 174-177.

Andreão, Rodrigo V. et al., "ECG Signal Analysis Through Hidden Markov Models," IEEE Transactions on Biomedical Engineering, vol. 53, No. 8, Aug. 2006, pp. 1541-1549.

Author Unknown, "Recommendations for measurement standard in quantitative electrocardiography," European Heart Journal: The CSE Working Party, vol. 6, No. 10, Oct. 1985, pp. 815-825.

Banerjee, Swati et al., "Application of Cross Wavelet Transform for ECG Pattern Analysis and Classification," IEEE Transactions on Instrumentation and Measurement, vol. 63, No. 2, Feb. 2014, pp. 326-333.

Barro, S. et al., "Algorithmic sequential decision-making in the frequency domain for life threatening ventricular arrhythmias and imitative artefacts: a diagnostic system," Journal of Biomedical Engineering, vol. 11, No. 4, Jul. 1989, pp. 320-328.

Bayasi, Nourhan et al., "Adaptive Technique for P and T Wave Delineation in Electrocardiogram Signals," 2014 36th Annual Conference of the IEEE Engineering in Medicine and Biology Society (EMBC), Aug. 26-30, 2014, Chicago, IL, pp. 90-93.

Bayasi, Nourhan et al., "Detection of Ventricular Arrhythmia Based on Unique ECG Parameters and Linear Discriminant Analysis," IEEE Transactions on Biomedical Engineering, 2014, 10 pages.

Clifford, Gari D., "Chapter 3: ECG Statistics, Noise, Artifacts, and Missing Data," Advanced Methods and Tools for ECG Data Analysis, Artech House, 2006, pp. 55-99.

Coast, Douglas A. et al., "QRS Detection Based on Hidden Markov Modeling," ECG Signal Processing II, 1989, IEEE, 2 pages.

De Azevedo Botter, Eduardo et al., "A Neural Network With Asymmetric Basis Functions for Feature Extraction of ECG P Waves," IEEE Transactions on Neural Networks, vol. 12, No. 5, Sep. 2001, pp. 1252-1255.

De Chazal, Philip et al., "Automatic Classification of Heartbeats Using ECG Morphology and Heartbeat Interval Features," IEEE Transactions on Biomedical Engineering, vol. 51, No. 7, Jul. 2004, pp. 1196-1206.

Elgendi, Mohamed et al., "Recognition of T Waves in ECG signals," 2009 IEEE 35th Annual Northeast Bioengineering Conference, Apr. 3-5, 2009, Boston, MA, 2 pages.

Fisher, R. A., "The Use of Multiple Measurements in Taxonomic Problems," Annals of Eugenics, vol. 1, No. 2, 1936, pp. 179-188.

Goldberger, Ary L. et al., "PhysioBank, PhysioToolkit, and PhysioNet: Components of a New Research Resource for Complex Physiologic Signals," Circulation, vol. 101, No. 2, Jun. 13, 2000, 7 pages.

Golpayegani, Glayol Nazari et al., "A novel approach in ECG beat recognition using adaptive neural fuzzy filter," Journal of Biomedical Science and Engineering, vol. 2, 2009, pp. 80-85.

Hamilton, Patrick S. et al., "Quantitative Investigation of QRS Detection Rules Using the MIT/BIH Arrhythmia Database," IEEE Transactions on Biomedical Engineering, vol. BME-33, No. 12, Dec. 1986, pp. 1157-1165.

Homaeinezhad, M.R. et al., "ECG arrhythmia recognition via a neuro-SVM-KNN hybrid classifier with virtual QRS image-based geometrical features," Expert Systems with Applications, vol. 39, 2012, pp. 2047-2058.

Jekova, Irena, "Shock advisory tool: Detection of life-threatening cardiac arrhythmias and shock success prediction by means of a common parameter set," Biomedical Signal Processing and Control, vol. 2, No. 1, 2007, pp. 25-33.

Khawaja, Antoun, "Automatic ECG Analysis Using Principal Component Analysis and Wavelet Transformation," Karlsruhe Transactions on Biomedical Engineering, vol. 3, Univ.-Verlag Karlsruhe, 2007, 234 pages.

(56) References Cited

OTHER PUBLICATIONS

Khushaba, Rami N. et al., "Driver Drowsiness Classification Using Fuzzy Wavelet-Packet-Based Feature-Extraction Algorithm," IEEE Transactions on Biomedical Engineering, vol. 58, No. 1, Jan. 2011, pp. 121-131.

Kligfield, Paul, "The Centennial of the Einthoven Electrocardiogram," Journal of Electrocardiography, vol. 35, No. 4, Part B, Oct. 2002, pp. 123-129.

Laguna, P. et al., "A Database for Evaluation of Algorithms for Measurement of QT and Other Waveform Intervals in the ECG," Computers in Cardiology, vol. 24, 1997, pp. 673-676.

Li, Qiao et al., "Ventricular Fibrillation and Tachycardia Classification Using a Machine Learning Approach," IEEE Transactions on Biomedical Engineering, vol. 61, No. 6, Jun. 2014, pp. 1607-1613.

Lin, Chao et al., "P- and T-Wave Delineation in ECG Signals Using a Bayesian Approach and a Partially Collapsed Gibbs Sampler," IEEE Transactions on Biomedical Engineering, vol. 57, No. 12, Dec. 2010, pp. 2840-2849.

Mallat, Stéphane, "A Wavelet Tour of Signal Processing," Academic Press, Second Edition, 1999, pp. 1-109.

Martínez, Juan Pablo et al., "A Wavelet-Based ECG Delineator: Evaluation on Standard Databases," IEEE Transactions on Biomedical Engineering, vol. 51, No. 4, Apr. 2004, pp. 570-581.

Mazomenos, E. B. et al., "A Time-Domain Morphology and Gradient based Algorithm for ECG Feature Extraction," 2012 IEEE International Conference on Industrial Technology (ICIT), Mar. 19-21, 2012, Athens, pp. 117-122.

Mazomenos, Evangelos B. et al., "A Low-Complexity ECG Feature Extraction Algorithm for Mobile Healthcare Applications," IEEE Journal of Biomedical and Health Informatics, vol. 17, No. 2, Mar. 2013, pp. 459-469.

Mehta, S. S. et al., "Detection of QRS complexes in electrocardiogram using support vector machine," Journal of Medical Engineering and Technology, vol. 32, No. 3, May/Jun. 2008, pp. 206-215.

Mehta, S. S. et al., "Recognition of P and T Waves in Electrocardiograms Using Fuzzy Theory," Proceedings of the First Regional Conference IEEE Engineering in Medicine and Biology Society and 14th Conference of the Biomedical Engineering Society of India, An International Meet, Feb. 15-18, 1995, New Delhi, pp. 2.54-2.55.

Murthy, I. S. N. et al., "Analysis of ECG from Pole-Zero Models," IEEE Transactions on Biomedical Engineering, vol. 39, No. 7, Jul. 1992, pp. 741-751.

Niknazar, Mohammad et al., "Fetal ECG Extraction by Extended State Kalman Filtering Based on Single-Channel Recordings," IEEE Transactions on Biomedical Engineering, vol. 60, No. 5, 2013, pp. 1345-1352.

Oweis, Rami J. et al., "Seizure classification in EEG signals utilizing Hilbert-Huang transform," Biomedical Engineering Online, vol. 10, No. 38, 2011, 15 pages.

Pal, Saurabh et al., "Empirical mode decomposition based ECG enhancement and QRS detection," Computers in Biology and Medicine, vol. 42, No. 1, Jan. 2012, pp. 83-92.

Pan, Jiapu et al., "A Real-Time QRS Detection Algorithm," IEEE Transactions on Biomedical Engineering, vol. BME-32, No. 3, Mar. 1985, pp. 230-236.

Pardey, J., "Detection of Ventricular Fibrillation by Sequential Hypothesis Testing of Binary Sequences," Computers in Cardiology, vol. 34, 2007, pp. 573-576.

Phyu, Myint Wai et al., "A Real-Time ECG QRS Detection ASIC Based on Wavelet Multiscale Analysis," IEEE Asian Solid-State Circuits Conference, 2009, A-SSCC 2009, Nov. 16-18, 2009, Taipei, Taiwan, pp. 293-296.

Sayadi, Omid et al., "Robust Detection of Premature Ventricular Contractions Using a Wave-Based Bayesian Framework," IEEE Transactions on Biomedical Engineering, vol. 57, No. 2, Feb. 2010, pp. 353-362.

Schleifer, J. William et al., "Ventricular Arrhythmias: State of the Art," Cardiology Clinics, vol. 31, No. 4, 2013, pp. 595-605.

Singh, Yogendra Narain et al., "ECG to Individual Identification," 2nd IEEE International Conference on Biometrics: Theory, Applications and Systems, 2008, BTAS 2008, Sep. 29-Oct. 1, 2008, Arlington, VA, 8 pages.

Sun, Yan et al., "Characteristic wave detection in ECG signal using morphological transform," BMC Cardiovascular Disorders, vol. 5, No. 28, 2005, 7 pages.

Tan, K. F. et al., "Detection of the QRS Complex, P Wave and T Wave in Electrocardiogram," First International Conference on Advances in Medical Signal and Information Processing, 2000, Bristol, pp. 41-47.

Zhang, Xu-Sheng et al., "Detecting Ventricular Tachycardia and Fibrillation by Complexity Measure," IEEE Transactions on Biomedical Engineering, vol. 46, No. 5, 1999, pp. 548-555.

Zong, W. et al., "A Robust Open-source Algorithm to Detect Onset and Duration of QRS Complexes," Computers in Cardiology, vol. 30, 2003, pp. 737-740.

Zong, W. et al., "Automated ECG Rhythm Analysis Using Fuzzy Reasoning," Computers in Cardiology, vol. 25, 1998, pp. 69-72.

Bayasi, Nourhan et al., "Low-Power ECG-Based Processor for Predicting Ventricular Arrhythmia," IEEE Transactions on Very Large Scale Integration (VLSI) Systems, vol. 24, No. 5, May 2016, pp. 1962-1974.

Non-Final Office Action for U.S. Appl. No. 14/926,483, dated Sep. 28, 2016, 8 pages.

Final Office Action for U.S. Appl. No. 14/926,483, dated Jan. 20, 2017, 7 pages.

Notice of Allowance for U.S. Appl. No. 14/926,483, dated Mar. 24, 2017, 11 pages.

Corrected Notice of Allowance for U.S. Appl. No. 14/926,483, dated Apr. 28, 2017, 4 pages.

Da Poian, G., et al., "Energy and Quality Evaluation for Compressive Sensing of Fetal Electrocardiogram Signals," Sensors 2017, vol. 17, No. 9, Dec. 22, 2016, 13 pages.

Mishra, A., et al., "ECG Signal Compression Using Compressive Sensing and Wavelet Transform," 34th Annual International Conference of the IEEE Engineering in Medicine and Biology Society, Aug. 28-Sep. 1, 2012, California, USA, 4 pages.

Polania, L. F., et al, "Compressed Sensing Based Method for ECG Compression," 2011 IEEE International Conference on Acoustics, Speech and Signal Processing (ICASSP), May 22-27, 2011, 4 pages.

Tawfic, I., et al., "Compressed Sensing of ECG Signal for Wireless System With New Fast Iterative Method," Computer Methods and Programs in Biomedicine, vol. 122, No. 3, Dec. 2015, 13 pages.

Yu, W., et al., "Adaptive compressive engine for real-time electrocardiogram monitoring under unreliable wireless channels," IET Communications, vol. 10, No. 6, Apr. 14, 2016, 9 pages.

Zhang, H., et al., "Implementation of Compressive Sensing in ECG and EEG Signal Processing," The Journal of China Universities of Posts and Telecommunications, vol. 17, No. 6, Dec. 2010, 5 pages.

Zhou, J., et al., "Asynchronous Binary Compressive Sensing for Wireless Body Sensor Networks," 2013 IEEE 9th International Conference on Mobile Ad-hoc and Sensor Networks, Dec. 11-13, 2013, 6 pages.

\* cited by examiner

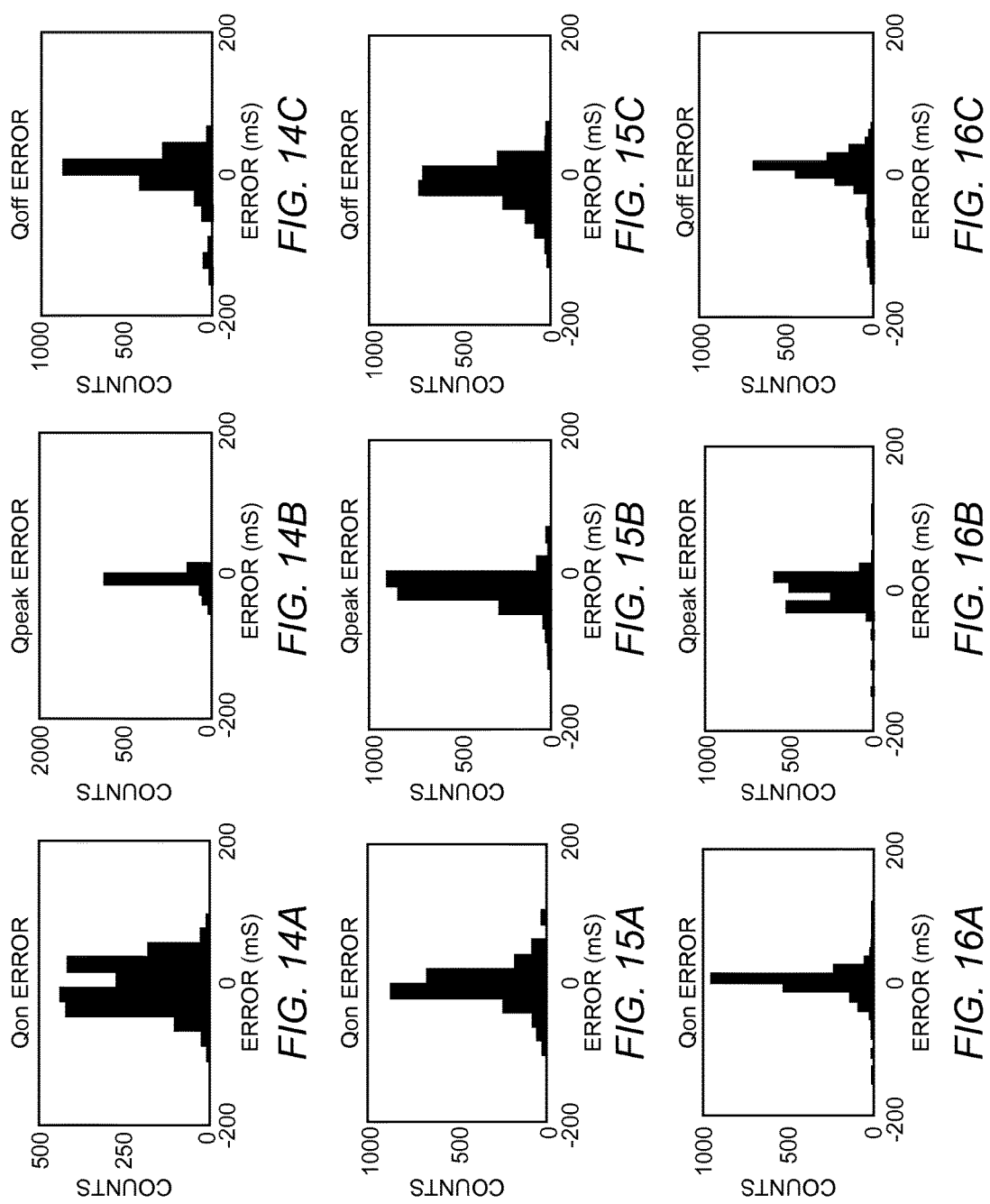

MEDICAL DEVICE HAVING AUTOMATED ECG FEATURE EXTRACTION

RELATED APPLICATIONS

This application claims the benefit of U.S. provisional patent application No. 62/069,975, filed Oct. 29, 2014, and 62/074,409, filed Nov. 3, 2014, the disclosure of which is incorporated herein by reference in its entirety.

FIELD OF THE DISCLOSURE

The present disclosure relates to biomedical devices and methods usable to monitor electrocardiogram signals.

BACKGROUND

The electrical activity of the heart is presented by the surface electrocardiogram (ECG) signal. Due to ease of use and non-invasiveness, ECG is not only used as a prime tool to monitor the functionality of the heart but also to diagnose cardiac arrhythmia by extracting information about intervals, amplitudes, and wave morphologies of the different P, QRS, and T waves. The extracted features from the ECG signal play an essential role in diagnosing many cardiac diseases. Hence, the development of real-time and accurate delineation methods is crucial, especially for abnormal ECG signals. Two main components of blocks can be classified, which are QRS detection and wave delineation.

A QRS complex, which is a principal component in the cardiac cycle, is used as a reference and represents the depolarization of ventricles in the heart. This amplitude rises to 1 mV or 2 mV above or below the isoelectric line for normal heartbeats and can be several times larger for abnormal heartbeats. The time required for the ventricles to depolarize defines the QRS width or interval and typically lasts between 80 ms and 120 ms.

In ECG signal analysis, accurate location of the position of the QRS complex is known as QRS detection and is a key to automatic techniques. The amplitude of the QRS complex is larger compared to the amplitude of the other waves that make up the ECG signal. As a result, detection processes for the QRS complex are easier in comparison. Various signal processing of QRS detection techniques have been proposed in literature. Time domain thresholding along with filtering such as first derivative, second derivative, both derivatives, and matched filter are some of the earliest techniques that are suitable for real-time implementation. Other methods that provide enhanced accuracy are based on spectral analysis of the ECG signal. For example, the wavelet transform is a tool to analyze ECG signals. As part of the spectral analysis techniques, the discrete Fourier transform has been reported in the literature to detect the QRS complex. Empirical mode decomposition and the Hilbert transform have been introduced to improve the analysis of the QRS detection of nonlinear and nonstationary ECG signals. Moreover, principal component analysis (PCA) that literally transforms the ECG data into a new coordinate system has been proposed in related art. QRS complex detection techniques could also be used with the concept of machine learning, classification, and pattern recognition. These QRS complex detection techniques are generally applicable when the QRS complex is used in the diagnosis of cardiac arrhythmia. QRS complex detection techniques include fuzzy logic, artificial neural network, neuro-fuzzy networks, support vector machine, and combinations of such techniques.

Delineation, which is the stage where fiducial points and the limits of the ECG waves are determined, is essential to the extraction of ECG parameters such as the ST interval and the QT interval. The localization of wave peaks is easier to detect than the onsets and offsets, as the signal-to-noise ratio is higher and becomes lower at the wave boundaries where the noise level dominates the ECG signal, which in turn leads to a complex delineation process. Generally, ECG wave delineation is performed after detecting the QRS complex where a set of search windows is defined to locate the T and the P wave. The search window enhances the characteristics of the targeted waves using different approaches proposed in related art literature.

A delineation technique based on the time curve derivative of digital signals is proposed in the related art. Adaptive filters and their different forms have also been used in the ECG delineation process. Time domain morphology and gradient, hidden Markov models, and Bayesian approaches along with the Gibbs sampler are other methods that offer a wide range of complexity, flexibility, accuracy, and cost. However, none of these related art delineation techniques are completely self-adaptive when performed by a medical device for the purpose of automated ECG feature extraction. Thus, there is a need for a medical device that provides self-adaptive automated ECG feature extraction.

SUMMARY

A medical device having automated ECG feature extraction is disclosed. The medical device includes input circuitry configured to receive an electrocardiogram (ECG) signal. Processing circuitry coupled to the input circuitry is configured to identify at least one fiducial point of a heartbeat signature within the ECG signal. The processing circuitry is further configured to perform substantially simultaneously both a discrete wavelet transform (DWT) and a curve length transform (CLT) to identify the at least one fiducial point.

In at least one embodiment, the processing circuitry is further configured to perform thresholding within the time domain. Moreover, the input circuitry is configured to perform band-pass filtering of the ECG signal.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure, and together with the description serve to explain the principles of the disclosure.

FIG. 14A is an error distribution bar graph for $Q_{on}$ error using DWT only.

FIG. 14B is an error distribution bar graph for $Q_{peak}$ error using DWT only.

FIG. 14C is an error distribution bar graph for $Q_{off}$ error using DWT only.

FIG. 15A is an error distribution bar graph for $Q_{on}$ error using extended CLT.

FIG. 15B is an error distribution bar graph for $Q_{peak}$ error using extended CLT.

FIG. 15C is an error distribution bar graph for $Q_{off}$ error using extended CLT.

FIG. 16A is an error distribution bar graph for $Q_{on}$ error using thresholding in the time domain.

FIG. 16B is an error distribution bar graph for $Q_{peak}$ error using thresholding in the time domain.

FIG. 16C is an error distribution bar graph for $Q_{off}$ error using thresholding in the time domain.

DETAILED DESCRIPTION

Figure 1:
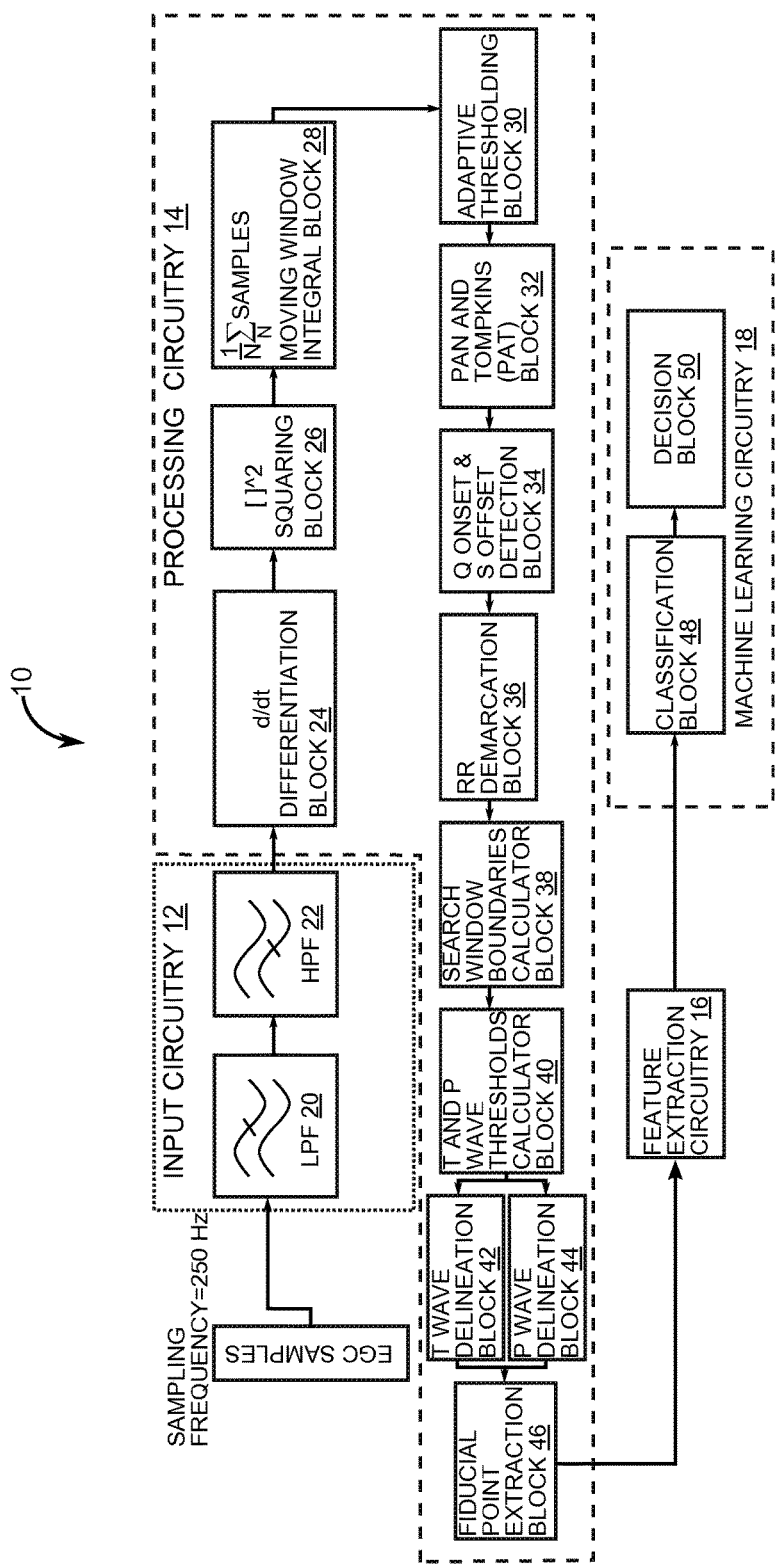
FIG. 1 is a schematic diagram depicting a medical device for monitoring electrocardiogram signals for ventricular arrhythmia events.

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

It will be understood that when an element such as a layer, region, or substrate is referred to as being "over," "on," "in," or extending "onto" another element, it can be directly over, directly on, directly in, or extend directly onto the other element or intervening elements may also be present. In contrast, when an element is referred to as being "directly over," "directly on," "directly in," or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

Section 1. Introduction

The present disclosure provides an analysis of performance for three ECG feature extraction methods after providing novel smart self-adaptive delineation methods that are implemented by a medical device of the present disclosure. One new method provided combines curve length transform (CLT) and discrete wave transform (DWT) in order to benefit from the advantages found in both CLT and DWT. Furthermore, DWT, time domain thresholding, and extended CLT are provided because the present analysis of performance has proven that these methods have powerful signal analysis capabilities favored for the extraction of ECG parameters. Traditional CLT and DWT type signal processing has been at the forefront of methods and have been found to be particularly useful in the study of ECG signals. However, for problematic and nonstationary signals, these methods alone are not capable of detecting and delineating fiducial points most of the time. In order to delineate fiducial points, the performance analysis provided by this disclosure has proven that delineation methods need to be self-adaptive in order to ensure high quality in robust processing of the ECG signal.

FIG. 1 is a schematic diagram depicting a medical device 10 of the present disclosure for detecting a ventricular arrhythmia event. In particular, the medical device 10 is a fully integrated ECG signal processing system suitable for real-time and efficient applications requiring detection of a ventricular arrhythmia event. Medical device 10 comprises input circuitry 12 that is configured to receive an ECG signal. Processing circuitry 14 is coupled to the input circuitry 12 and is configured to identify at least one fiducial point of a first heartbeat signature and at least one fiducial point of a second heartbeat signature. Each of the at least one fiducial point is associated with at least one of six ECG parameters that include PQ interval variability, QP interval variability, RT interval variability, TR interval variability, PS interval variability, and SP interval variability. However, it is to be understood that the each of the at least one fiducial point is not limited to just the six ECG parameters listed above. Other ECG parameters such as upper and lower envelope variations are also usable.

Feature extraction circuitry 16 is coupled to the processing circuitry 14 and is configured to determine at least one difference between the at least one fiducial point of the first heartbeat signal and the at least one fiducial point of the second heartbeat signal. Machine learning circuitry 18 is coupled to the feature extraction circuitry 16 and is configured to select a ventricular arrhythmia class based on the at least one difference.

In more detail, the input circuitry 12 includes a low-pass filter 20 and a high-pass filter 22 that are configured to remove unwanted noise signals coupled within the ECG signal. Once filtered, the ECG signal is received by the processing circuitry 14, which includes a differentiation block 24 that takes a derivative of the filtered ECG signal. A squaring block 26 is configured to square the derivative of the filtered ECG signal before a moving window integral block 28 integrates data samples within the ECG signal that contains at least two QRS complexes, two P waves and two T waves from at least two heartbeat signatures. An adaptive thresholding block 30 is configured to locate the two or more QRS complexes. A Pan and Tompkins (PAT) block 32 is configured to locate the R peaks within the QRS complexes once the adaptive thresholding block 30 provides demarcation of the QRS complex. A Q onset and S offset detection block 34 is configured to search and detect Q onsets and S offsets for each of the QRS complexes demarcated.

An RR demarcation block 36 is configured to determine the interval between two R peaks detected by the PAT block 32. Typically, the two R peaks are automatically selected from two consecutive heartbeat signatures. A search window boundaries calculator block 38 is configured to perform calculations to determine search window boundaries that will contain T wave and P wave fiducial points. The calculations performed take into consideration the sampling frequency of the ECG signal. For instance, the search window boundaries may select more sample points for a higher frequency ECG sampling. While FIG. 1 depicts the ECG sampling frequency as being 250 Hz, other sampling frequencies such as 360 Hz are usable with the search window boundaries calculator block 38.

A T and P wave thresholds calculator block 40 is configured to calculate amplitude thresholds for the T waves and the P waves within the window boundaries calculated by the search window boundaries calculator block 38. A T wave delineation block 42 is configured to determine a precise location for each of the T waves using T wave amplitude thresholds received from the T and P wave amplitude thresholds calculator block 40. Similarly, a P wave delineation block 44 is configured to determine a precise location for each of the P waves using P wave amplitude thresholds received from the T and P wave thresholds calculator block 40.

A fiducial point extraction block 46 is configured to find fiducial points within the calculated search window boundaries. The fiducial points extracted can be but are not limited to P peak, P offset, Q onset, R peak, S offset, T peak and T offset. Medical device 10 along with the following disclosed techniques take into account different ECG waveform morphologies and utilize adaptive search windows along with thresholds to accurately detect the fiducial points of each heartbeat.

In an exemplary embodiment, the feature extraction circuitry 16 is configured to extract six parameters from search windows placed within the ECG signal. In this exemplary embodiment, the search window size is around five seconds of an ECG signal. Once features are extracted, various other unique combinations of the parameters are constructed and used as input for the machine learning circuitry 18, which includes a classification block 48 that is configured to classify the extracted features and a decision block 50 that is configured to determine if a ventricular arrhythmia event is occurring based upon the classification of the extracted features.

Section 2. Methods Based on Discrete Wavelet Transform

Section 2.1. Discrete Wavelet Transform

Wavelet transform (WT) provides both time and frequency information without resolving all frequencies equally. At high frequencies, WT provides good time resolution and poor frequency resolution while it does the opposite at low frequencies. Thus, WT is a useful tool when the signal has high-frequency components for short duration and low-frequency components for long duration. ECG signals have low-frequency components for relatively long durations. WT has been widely used and has become an important tool to analyze the ECG signal and delineate its fiducial points.

WT provides decomposition of a signal over a set of basic functions obtained by dilation and translation of a mother wavelet. Dilation is governed by a scale factor $\alpha$ and a translation parameter $\beta$. The WT of a signal x(t) is given by equation 1.

$$W_\alpha x(b) = \frac{1}{\sqrt{\alpha}} \int x(t) \phi\left(\frac{t-b}{\alpha}\right) dt \quad (1)$$

Figure 2:
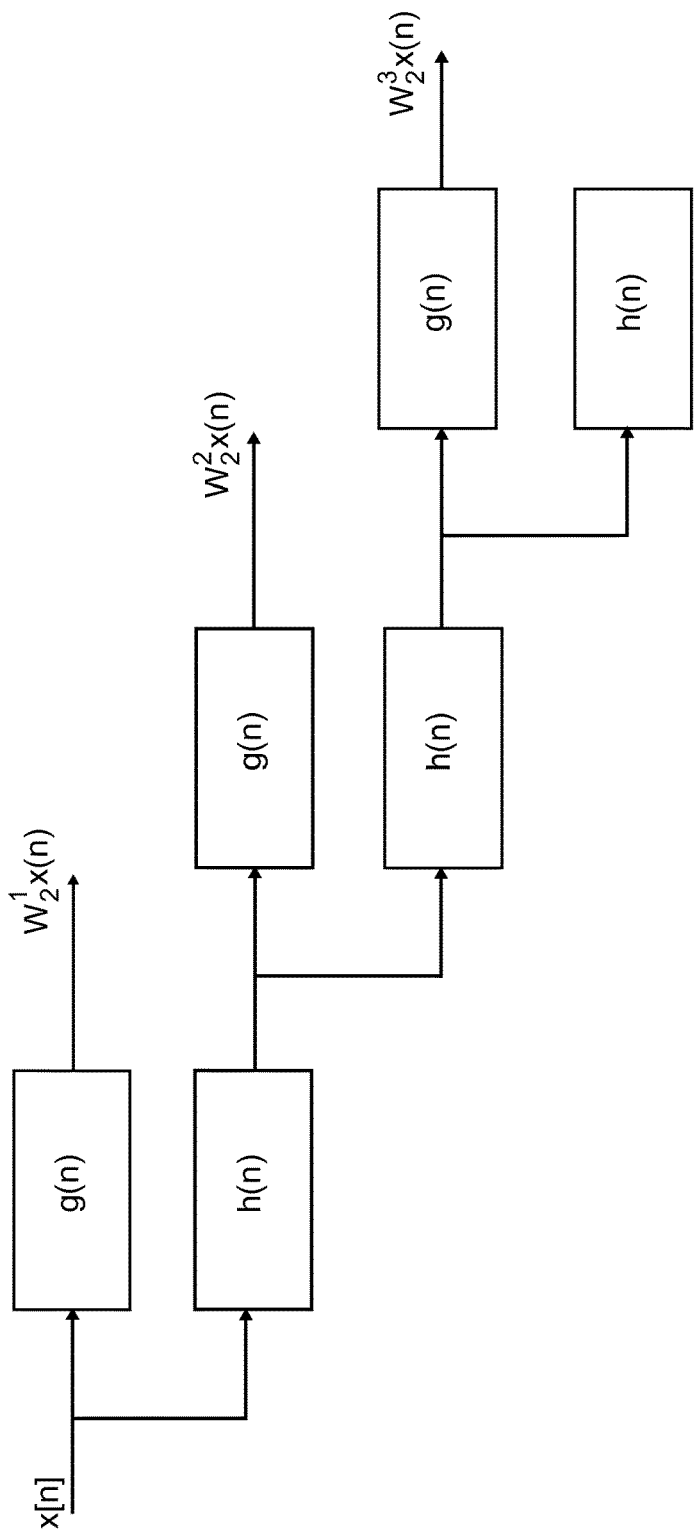
FIG. 2 is a block diagram of two filter-bank implementation of a discrete wavelet transform (DWT) implementation without decimation of the trous algorithm.

The DWT is implemented as an octave filter bank by cascading low pass and high pass filters. In order to keep the temporal resolution at different scales, algorithme á trous is implemented as shown in FIG. 2, where h[n] and g[n] are given in equation 2 and equation 3, respectively.

$$h[n] = \frac{1}{2}[\delta[n+2] + \delta[n+1] + \delta[n] + \delta[n-1]] \quad (2)$$

$$g[n] = 2[\delta[n+1] - \delta[n]] \quad (3)$$

A mother wavelet based on a quadratic spline wavelet is selected due to its ease of implementation and accuracy for analyzing ECG signals. The Fourier transform of the selected mother wavelet is given in equation 4.

$$\Phi(\Omega) = j\Omega \left( \frac{\sin\left(\frac{\Omega}{4}\right)}{\frac{\Omega}{4}} \right)^4 \quad (4)$$

Section 2.2. Detection and Delineation of ECG Signals Based on WT

An ECG signal is coupled with different forms of noise such as baseline wander, sudden body movement, and line power ripple. Unlike other ECG detection and delineation methods, WT suppresses noise in a single step without a need for pre-filtering. Different ECG components are visible at different DWT scales and a zero crossing of maximum modulus pair (MMP) across the scales correspond to fiducial points.

Section 2.2(a) QRS Complex Detection and Delineation

QRS complex detection is based on a search window approach. A search window of four seconds is designed to search for the QRS complex. When a QRS complex is detected a blocking window of 200 ms is utilized before searching the next peak. Significant slopes of the QRS complex are associated with the maximum of MMP in $|W_2^3 x[n]|$. A zero crossing of MMP corresponds to an R peak. Q onset and Q offset are at the edge of the slopes before and after the R peak. A pair of maximum modulus lines at scale before and after the R peak corresponds to the Q wave and S wave respectively. An MMP is classified to correspond to an R peak, a Q onset, or a Q offset based on predetermined thresholds for R peak voltage $\vartheta_R$, Q onset voltage $\vartheta_{Qon}$, and Q offset voltage $\vartheta_{Qoff}$ that are given in equations 5, 6, and 7, respectively.

$$\vartheta_R = 1.5 RMS(win_{RR}|W_2^3 x[n]|) \quad (5)$$

$$\vartheta_{Qon} = 0.1 \vartheta_R \quad (6)$$

$$\vartheta_{Qoff} = 0.1 \vartheta_R \quad (7)$$

When $\vartheta_R$ changes, $\vartheta_{Qon}$ and $\vartheta_{Qoff}$ are consequently updated in each heartbeat. A temporal window is defined before and after the R peak and the thresholds are applied to search for Q onset and Q offset. FIGS. 3A through 3F illustrate two examples of QRS complex detection based on DWT across the first scale and the second scale.

Figure 3D:
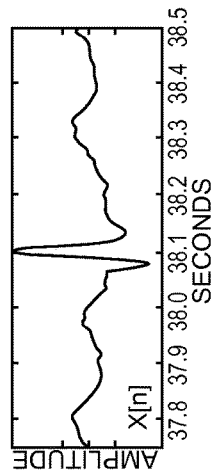
FIG. 3D is a graph of a second portion of an incoming ECG signal X[n] that has yet to be processed.
Figure 3E:
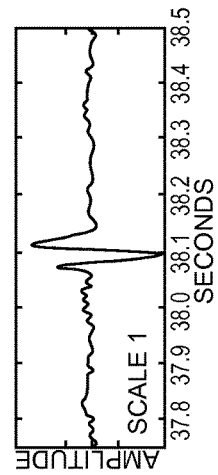
FIG. 3E is a graph of the ECG signal X[n] of FIG. 3D that has been processed at scale 1.
Figure 3F:
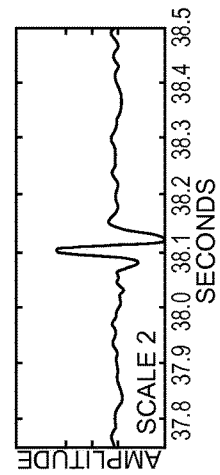
FIG. 3F is a graph of the ECG signal X[n] of FIG. 3D that has been processed at scale 2.
Figure 3A:
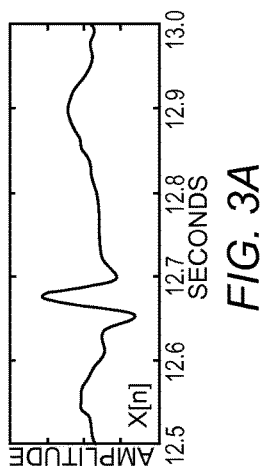
FIG. 3A is a graph of a first portion of an incoming ECG signal X[n] that has yet to be processed.
Figure 3B:
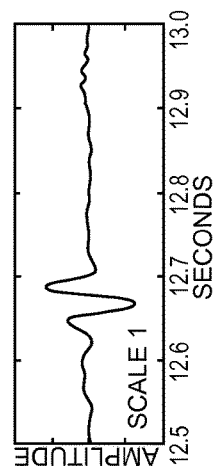
FIG. 3B is a graph of the ECG signal X[n] of FIG. 3A that has been processed at scale 1.
Figure 3C:
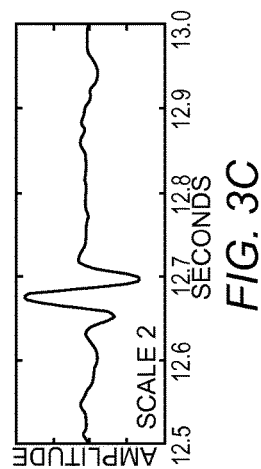
FIG. 3C is a graph of the ECG signal X[n] of FIG. 3A that has been processed at scale 2.

FIG. 3A is a graph of a first portion of an incoming ECG signal X[n] that has yet to be processed. FIG. 3B is a graph of the ECG signal X[n] of FIG. 3A that has been processed at scale 1. FIG. 3C is a graph of the ECG signal X[n] of FIG. 3A that has been processed at scale 2. FIG. 3D is a graph of a second portion of an incoming ECG signal X[n] that has yet to be processed. FIG. 3E is a graph of the ECG signal X[n] of FIG. 3D that has been processed at scale 1. FIG. 3F is a graph of the ECG signal X[n] of FIG. 3D that has been processed at scale 2.

Section 2.2(b) T and P Wave Delineation

A T wave is representative of repolarization of ventricles whereby the myocardium is prepared for another cycle, while the P wave is representative of repolarization of the atria. Automatic delineation of an ECG signal is concerned with the onset and offset of various waveforms such as the T waveform and the P waveform. Of particular interest are measurements determining when the T wave ends and in particular, the detection of the T offset. The detection of the T offset is typically the most difficult to locate among the ECG fiducial points, mainly due to a slow transition of the signal near the end of the T wave. In addition, T waves have oscillatory patterns that vary from one individual to another, which makes the delineation process even more challenging. After the QRS detection, two search windows at scale $2^4$ are defined depending on the location of the QRS complex and the previously computed RR interval that is the time between consecutive R peaks.

The search windows typically have different sizes in order to search for the T wave and the P wave separately. A T wave is located in $win_T$ if MMP exists in $|W_2^4 x[n]|$ and the local maxima exceeds a threshold $\vartheta_T$. Similarly, a P wave is identified within the window $win_P$ if MMP exists in $|W_2^4 x[n]|$ and maxima points exceed a threshold $\vartheta_P$. T wave and P wave threshold levels are given in equation 8 and equation 9, respectively.

$$\vartheta_T = RMS(win_T|W_2^4 x[n]|) \quad (8)$$

$$\vartheta_P = RMS(win_P|W_2^4 x[n]|) \quad (9)$$

The wave boundaries are identified by looking at the positive maxima and the negative minima of their respective MMP. A zero crossing of their MMPs are mapped to their respective peaks. A delay due to higher scales is also taken into account when mapping to an original ECG signal. Examples of T wave and P wave delineation of different morphologies are illustrated in FIGS. 4A through 4F.

Figure 4A:
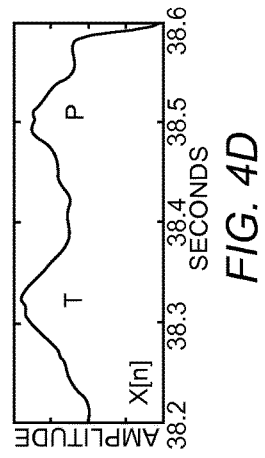
FIG. 4A is a graph of a first portion of an incoming ECG signal X[n] that has yet to be processed.
Figure 4B:
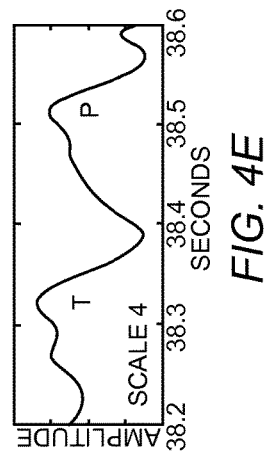
FIG. 4B is a graph of the ECG signal X[n] of FIG. 4A that has been processed at scale 4.
Figure 4C:
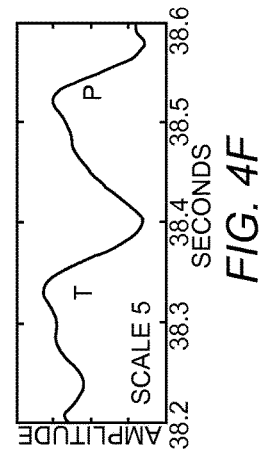
FIG. 4C is a graph of the ECG signal X[n] of FIG. 4A that has been processed at scale 5.
Figure 4D:
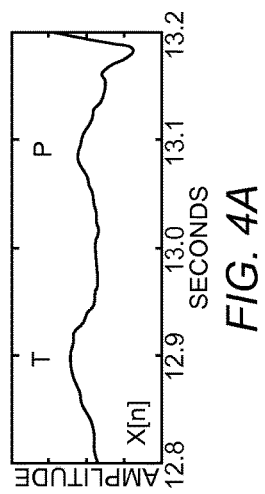
FIG. 4D is a graph of a second portion of an incoming ECG signal X[n] that has yet to be processed.
Figure 4E:
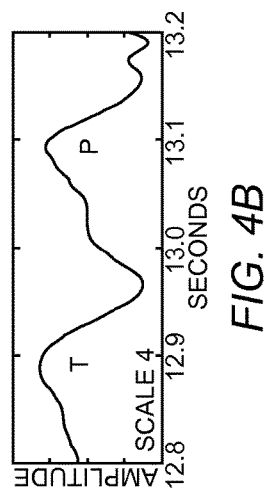
FIG. 4E is a graph of the ECG signal X[n] of FIG. 4D that has been processed at scale 4.
Figure 4F:
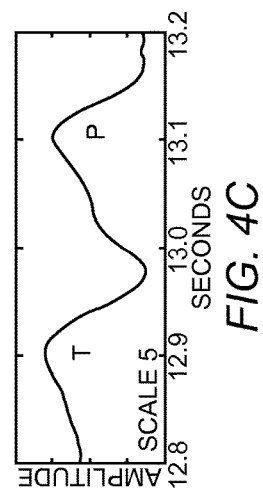
FIG. 4F is a graph of the ECG signal X[n] of FIG. 4D that has been processed at scale 5.

FIG. 4A is a graph of a first portion of an incoming ECG signal X[n] that has yet to be processed. FIG. 4B is a graph of the ECG signal X[n] of FIG. 4A that has been processed at scale 4. FIG. 4C is a graph of the ECG signal X[n] of FIG. 4A that has been processed at scale 5. FIG. 4D is a graph of a second portion of an incoming ECG signal X[n] that has yet to be processed. FIG. 4E is a graph of the ECG signal X[n] of FIG. 4D that has been processed at scale 4. FIG. 4F is a graph of the ECG signal X[n] of FIG. 4D that has been processed at scale 5.

Section 3. Methods Based on Extended Curve Length Transform

Section 3.1. Curve Length Transform

A curve length transform (CLT) provides a computationally efficient ECG detection technique. CLT is used to determine lengths between successive points of an ECG signal thereby providing a way to characterize the features that deviate from a baseline. Since the transform is sensitive to spikes due to noise, the ECG signal is filtered before being processed by the CLT. The QRS complex is enhanced through CLT processing while other features are suppressed by employing a window size equivalent to the duration of the QRS complex. The length of a curve of a continuous signal y(t) and a discrete signal $y_i$ over a time window w is defined as L, which is given in equations 10 and 11, respectively.

$$L(\omega, t) = \int_{t-\omega}^{t} \sqrt{1 + \left(\frac{dy}{dt}\right)^2} \, dt \quad (10)$$

$$L(\omega, i) = \sum_{t-\omega}^{t} \sqrt{1 + \left(\frac{\Delta y_k}{\Delta t}\right)^2} \, \Delta t \quad (11)$$

CLT can be re-written and evaluated as given in equation 12 and equation 13.

$$L(\omega, t) = \int_{t-\omega}^{t} \sqrt{C^2 + d_y^2} \quad (12)$$

$$L(\omega, i) = \sum_{t-\omega}^{t} \sqrt{C^2 + \Delta y^2} \quad (13)$$

The term $\Delta t^2$ corresponds to the square of the sampling period which is a constant value that is replaced with a nonlinear scaling factor $C^2$. The nonlinear scaling factor $C^2$ adds flexibility to manipulate the length response ratio. The nonlinear scaling factor $C^2$ is determined by taking into account window size along with the maximum height of the QRS complex. By choosing an appropriate value for the nonlinear scaling factor $C^2$, a predetermined portion of the signal is amplified relative to the remainder of the ECG signal. Statistical values based on the wave response of the ECG signal can be used to enhance the QRS complex, the T wave and the P wave.

Figure 5:
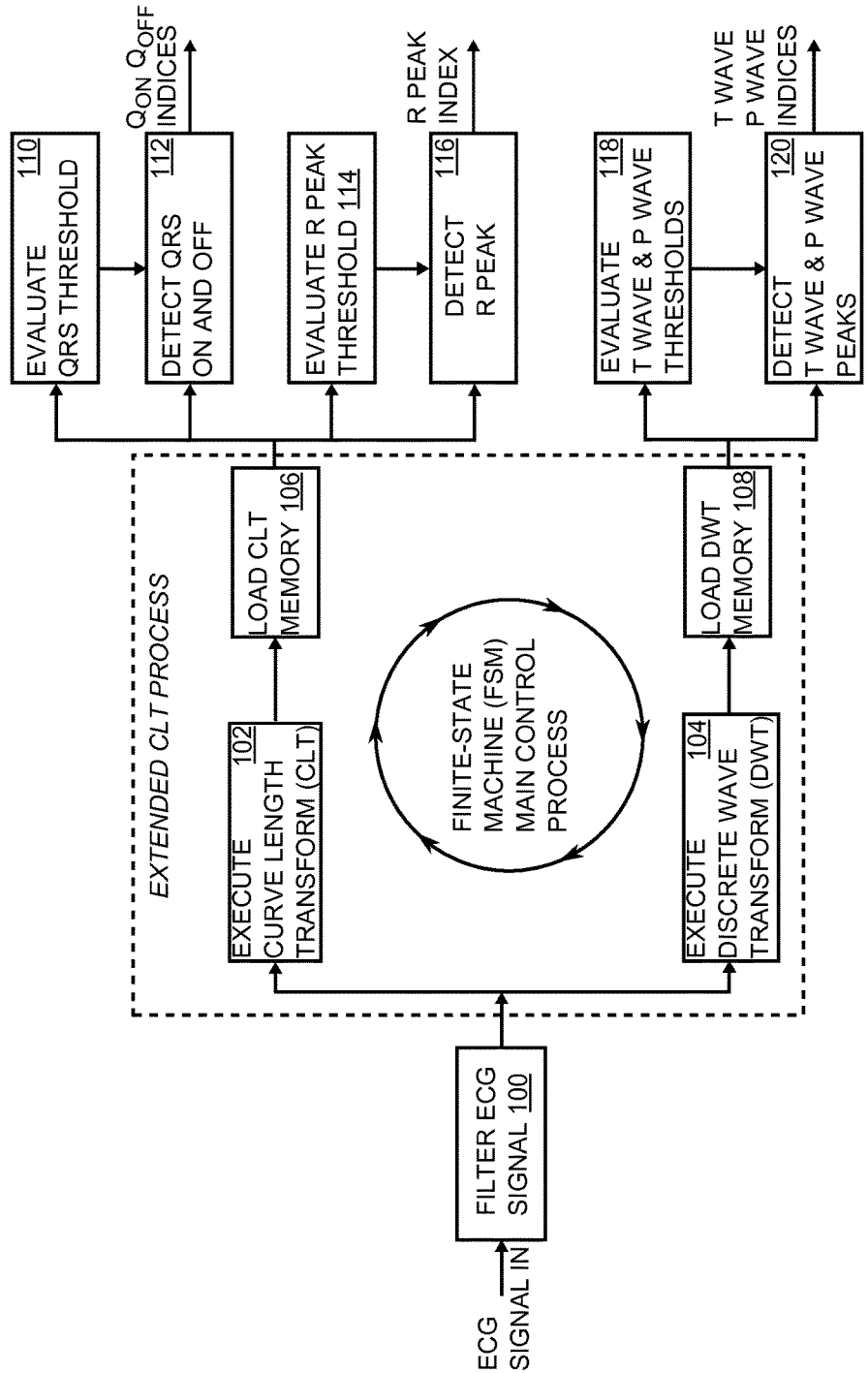
FIG. 5 is a block diagram that depicts a process for implementing extended CLT in accordance with the present disclosure.
Figure 6:
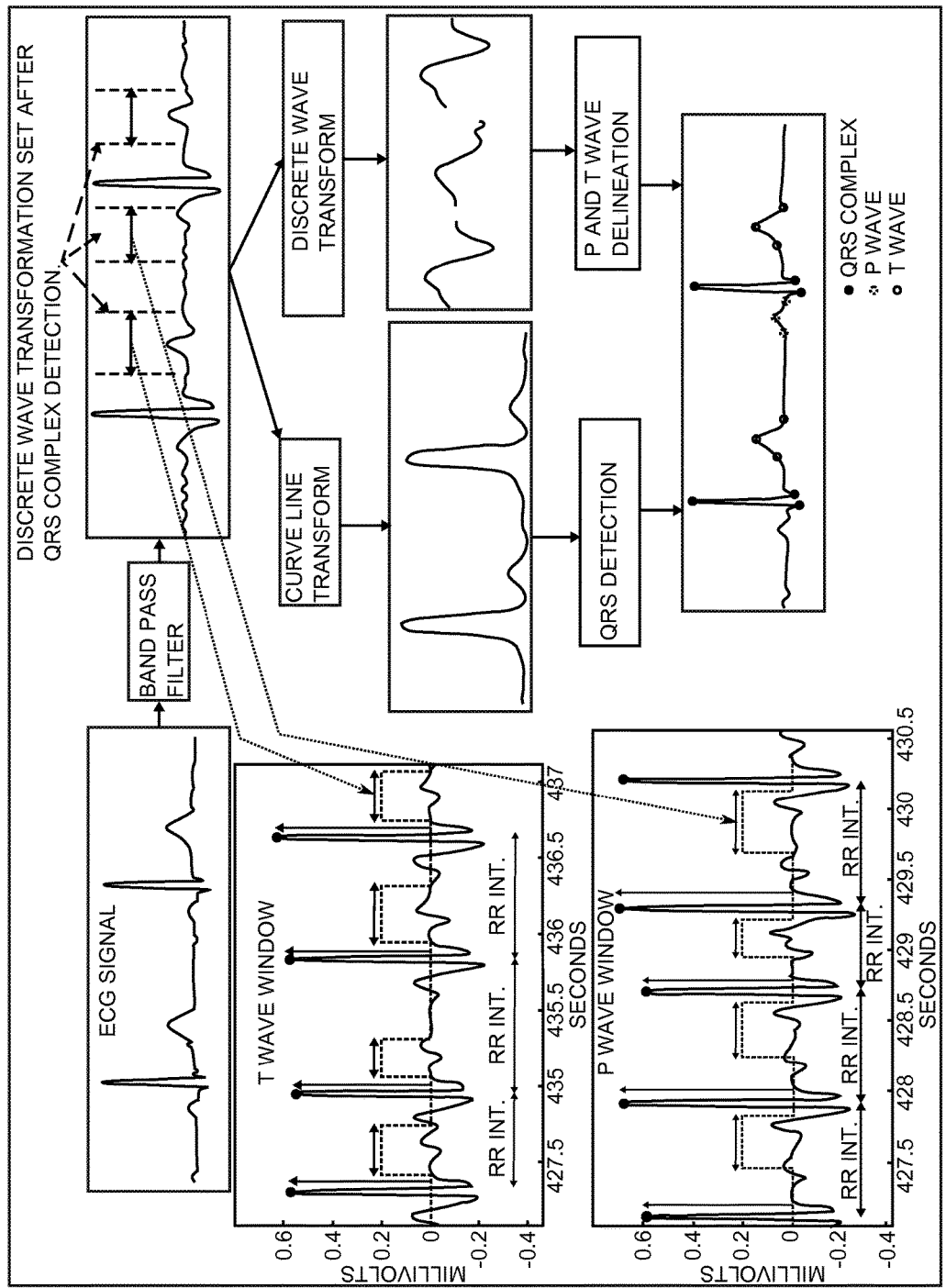
FIG. 6 is a sequential ECG signal processing results diagram showing results generated from the process including extended CLT as depicted in FIG. 5.

FIG. 5 is a block diagram that depicts a process for implementing extended CLT in accordance with the present disclosure. The extended ECG process begins with filtering an incoming ECG signal (step 100). After filtering, a CLT is executed (step 102). Practically simultaneously, a DWT is executed (step 104). Output from the CLT is loaded into memory such as random access memory (RAM) (step 106). Nearly simultaneously, output from the DWT is loaded into memory such as RAM (step 108). Data from the CLT-loaded memory feed blocks that evaluate the QRS threshold (step 110), detect the QRS on and off (step 112), evaluate the R peak threshold (step 114), and detect the R peak (step 116). Practically simultaneously, data from the DWT feed blocks that evaluate the T wave and P wave thresholds (step 118) and detect the T wave and P wave peaks (step 120). FIG. 6 is sequential ECG signal processing results diagram showing results generated from the process including extended CLT as depicted in FIG. 5.

Section 3.2. Detection and Delineation of ECG Signal Based on CLT

A preprocessing stage reduces noise and baseline wandering before performing CLT. The preprocessing stage comprises a band-pass filter that reduces low frequency components of baseline wandering, line power ripple, and high frequency noise. Following filtering, the CLT is applied to the ECG signal by selecting an appropriate search window size and scale factor. In an exemplary embodiment, the search window size is set to 128 ms in order to enhance a QRS complex without including an adjacent T wave and an adjacent P wave. A resulting CLT-processed signal is utilized to locate and delineate the QRS complex while a DWT is employed to generate T wave and P wave averages from the filtered ECG signal.

Section 3.3 QRS Complex Detection and Delineation

QRS complex detection comprises a step of automatically invoking the adaptive thresholding block 30 to locate peaks within the QRS complex and locating ends of the QRS complex to the left and right of located peaks within a search window. A threshold value $Th_{up}$ is adaptive where its initial value is set at a mean of 4 seconds of the CLT processed signal. When a new QRS complex peak is detected, the threshold value is updated to two-thirds the sum of the threshold and the CLT processed signal of a previous heartbeat signature within the ECG signal. Equation 14 gives a mathematical expression for calculating the threshold value $Th_{up}$.

$$Th_{up} = \tfrac{2}{3}[\text{mean}(CLT_{Prebeat}) + Th_{pre}] \quad (14)$$

As a result of equation 14, the threshold value $Th_{up}$ keeps track of the amplitude of an incoming CLT processed signal, which avoids a need for a backwards search. Once the CLT processed signal crosses the threshold value $Th_{up}$, a next peak is recognized by the adaptive thresholding block 30 and is recorded by the adaptive threshold block 30 as a QRS complex peak.

A local search window starting a threshold-crossing point is defined to delineate the Q onset and the Q offset. Processor instructions executed by the adaptive thresholding block 30 sets a local minimum value $L_{min}$ in a backward window of 64 ms and a local maximum value $L_{max}$ in a forward window of 64 ms. A difference $L_{diff}=L_{max}-L_{min}$ is used to evaluate additional thresholds $Th_{Qon}$ and $Th_{Qoff}$ given in equation 15 and equation 16, respectively.

$$Th_{Qon} = 1.4 L_{min} + \frac{L_{diff}}{10} \quad (15)$$

$$Th_{Qoff} = L_{max} - \frac{L_{diff}}{10} \quad (16)$$

Section 3.4 T Wave and P Wave Average Delineation

Self-adaptive search windows after and before the QRS complex in the filtered ECG signal are defined as locations of the T wave and the P wave, respectively. The boundaries of the search windows are set to be adaptive and relative to the position of the QRS complex location and the RR interval. During each heartbeat signature, the RR demarcation block 36 computes the RR interval and accordingly updates the size of the search window. The forward search window contains the T wave boundaries and is extended from the Q offset to two-thirds of the previous RR interval, whereas the backward window contains the P peak and is extended from the Q onset to two-thirds of the previous RR interval. The windowed signals are transformed using DWT. The T wave and the P wave limits are obtained as described previously with the exception that a DWT at scale 3 is used. The thresholds are updated by taking the mean of the windowed signal and the MMP recognition method is applied. In the exemplary embodiment of FIG. 5, a combination of CLT and DWT in the form of extended CLT provides substantially improved performance in accuracy and efficiency in comparison to prior art and related art methods.

Figure 7:
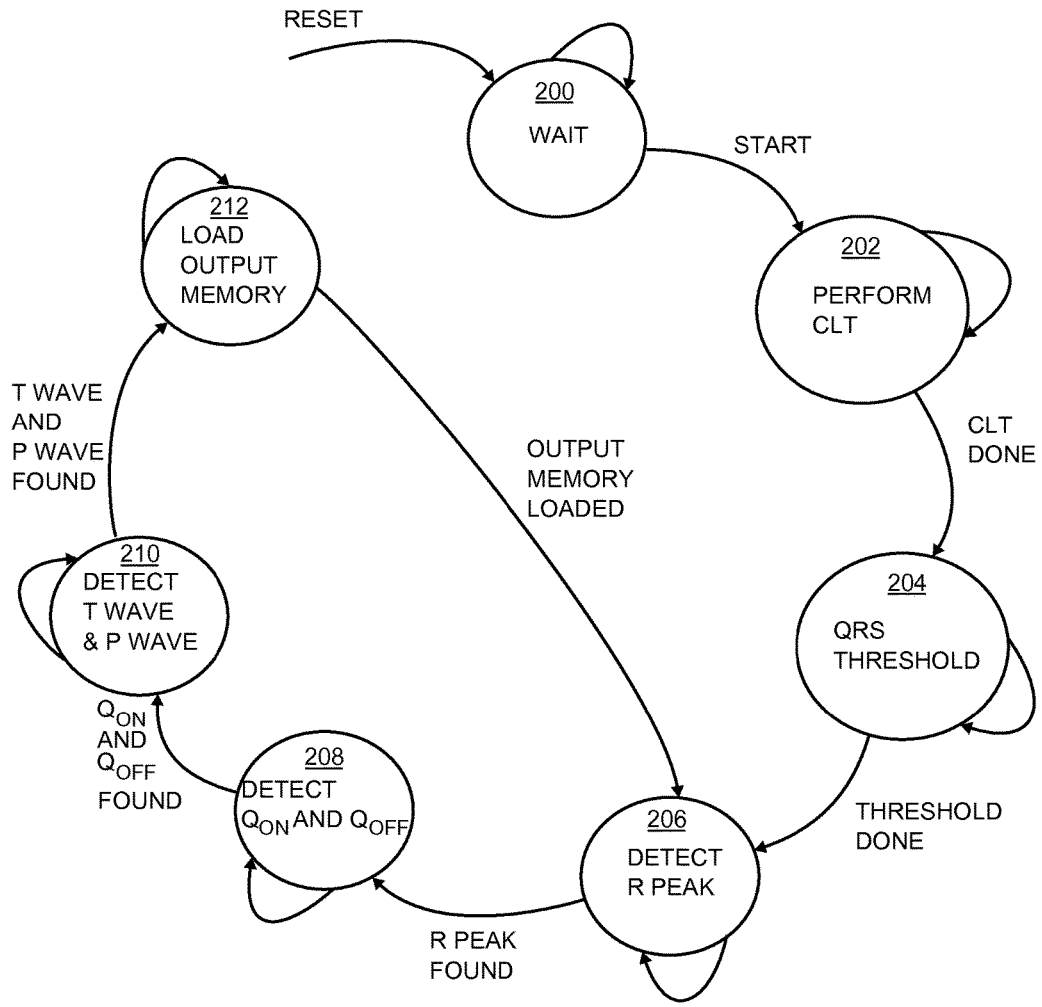
FIG. 7 is a diagram of the finite-state machine (FSM) main control process for the extended CLT process of FIG. 5.

FIG. 7 is a diagram of the finite-state machine (FSM) main control process for the extended CLT process of FIG. 5. The process begins with waiting for an incoming ECG signal (step 200). Once an ECG signal arrives, the process performs a CLT on the incoming ECG signal (step 202). Next, a QRS threshold is established using the CLT results (step 204). The R peak is then detected (step 206). Then Q onset and Q offset are detected (step 208). Next, the T wave and the P wave are detected (step 210). Output memory is then loaded with the located R peak location, the Q onset and Q offset locations, and the T wave and P wave locations (step 212). The process continues by repeating steps 206-212 until a reset occurs.

Figure 8:
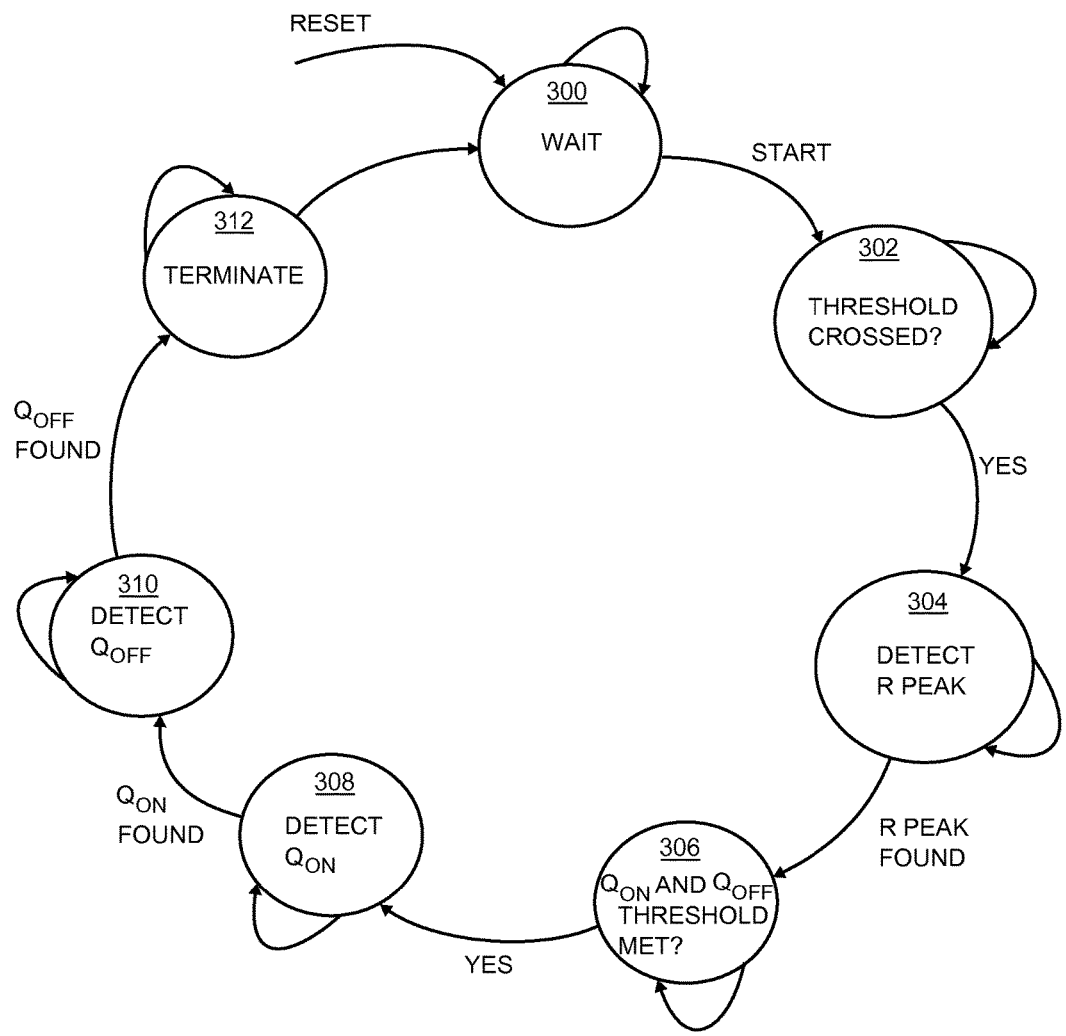
FIG. 8 is a diagram of an FSM control process for QRS detection.

FIG. 8 is a diagram of an FSM control process for QRS detection. The process begins with waiting for an incoming CLT-processed ECG signal (step 300). Once the CLT-processed ECG signal arrives, a test is conducted to determine if a QRS threshold has been reached (step 302). Once a QRS threshold is crossed, the R peak is detected (step 304). Then a test is conducted to determine if a Q onset threshold and a Q offset threshold have been met (step 306). If so, the Q onset is detected (step 308). Then the Q offset is detected (step 310) after which the process is terminated (step 312). A new process begins with either a reset or a wait (step 300).

Figure 9:
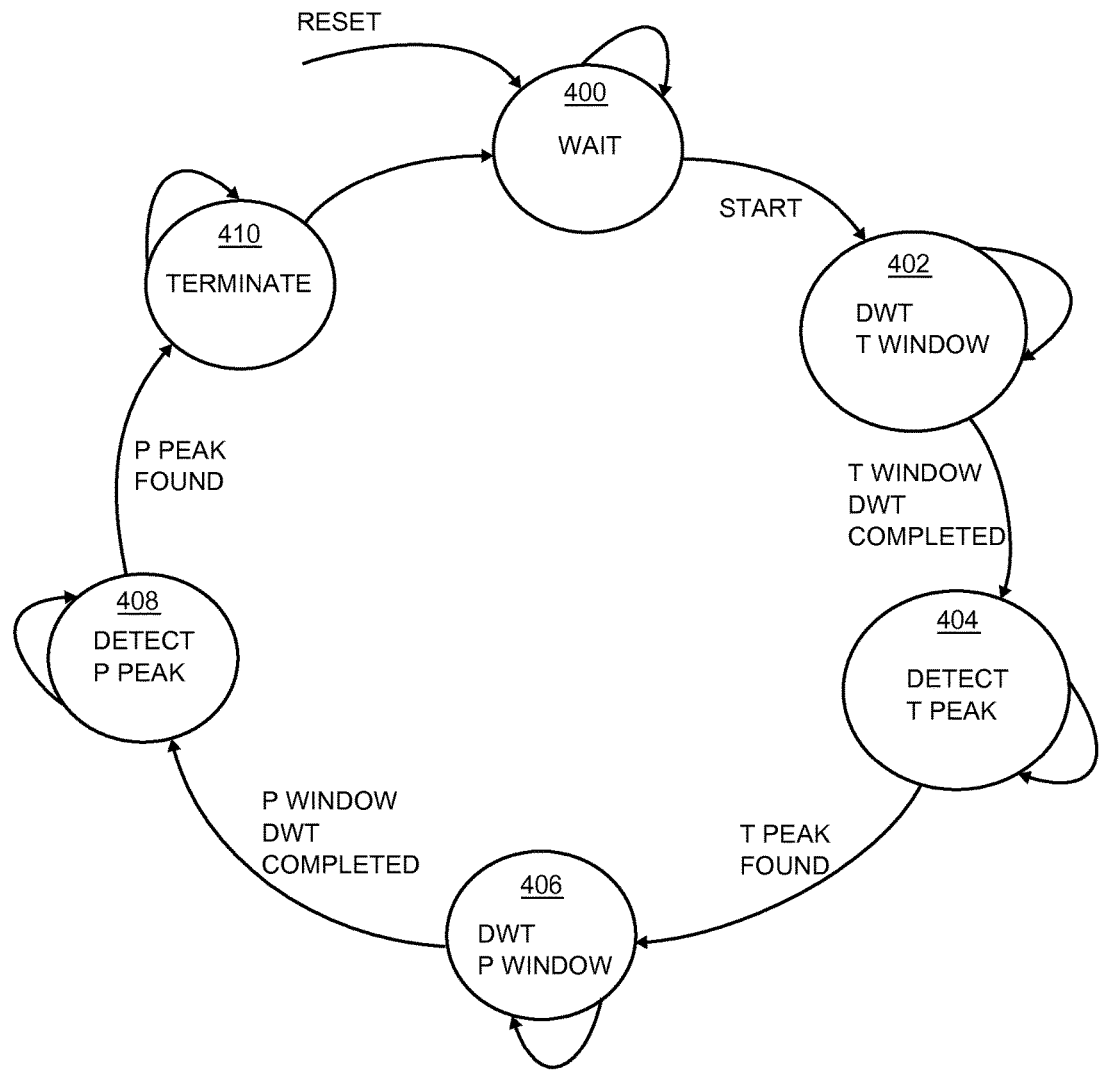
FIG. 9 is a diagram of an FSM control process for the delineation of the T wave and the P wave.

FIG. 9 is a diagram of an FSM control process for the delineation of the T wave and the P wave. The process begins with waiting for an incoming DWT-processed ECG signal (step 400). Once a DWT-processed ECG signal is received, a DWT T window is established (step 402). A T peak is then located within the DWT window (step 404). Next, a DWT P window is established (step 406) to facilitate detecting a P peak within the DWT P window (step 408). The present process terminates once the P peak is located (step 410) and a new process begins with either a reset or a wait (step 400). FIG. 9 is exemplary in showing that the P peak and T peak are located sequentially. However, it is to be understood that the P peak and the T peak can be located in parallel since their respective thresholds and windows are independent of each other.

Section 4. Methods Based on Time Domain Thresholding

Section 4.1. Pan and Tompkins Block

A widely used concept of real-time QRS detection is based on amplitude threshold that exploits a fact that R peaks have higher amplitudes compared to other ECG wave peaks. However, the ECG signal is always combined with noise that typically limits the accuracy and sensitivity of thresholding techniques. In an exemplary embodiment, the Pan and Tompkins (PAT) block 32 (FIG. 1) is used for enhancement and detection of the QRS complex. The PAT block 32 employs slope, amplitude, and width measurements of an ECG signal in order to successfully detect the R peak of the QRS complex.

Section 4.2. Detection and Delineation of ECG Signal Based on PAT

The PAT block 32 provides real-time QRS complex detection that is implemented in six stages as shown in FIG. 1. The linear filters LPF 20 and HPF 22 are used to remove noise within ECG signals that come from power lines and other noise sources. Filtering is typically needed to prevent undesirable detection of noise peaks within an ECG signal by the PAT block 32. Nonlinear transformation of the ECG signal is used to enhance the QRS complex and suppress the T wave and the P wave. In an exemplary embodiment, the nonlinear transformation is performed by the differentiation block 24, the squaring block 26, and the moving window integral block 28.

Section 4.3 QRS Complex Detection and Delineation

The adaptive thresholding block 30 that is used to detect the QRS complex depends upon continuously updated estimates of the peak signal level and the peak noise level. The signal to noise ratio (SNR) of the ECG signal increases as the ECG signal passes through the input circuitry 12 that includes the LPF 20 and the HPF 22 and provides a bandpass filter function. As a result of increased SNR, thresholds are more readily applied to generate accurate peak detection of the QRS complex. However, traditional thresholding techniques are not self-adaptive and are not reliably suitable for real-time implementation of QRS complex detection and delineation. The present disclosure provides modifications to traditional peak detection techniques that yield improvements necessary for real-time QRS complex detection and delineation.

In this regard, the present adaptive thresholding block 30 is initialized without any threshold levels set. Instead, an absolute maximum value $R_{peak}$ within a first search window is set to the peak amplitude of the R peak. An initial threshold value of 50% of $R_{peak}$ is then set. Next, the adaptive thresholding block 30 establishes a first adaptive threshold value $Th_1$ and a second adaptive threshold value $Th_2$. After each heartbeat signature, the first adaptive threshold value $Th_1$ and a second adaptive threshold value $Th_2$ each change in value depending on peak amplitude values recorded from previously detected peaks.

The first adaptive threshold value is given by equation 17 and is simply 50% of the previously detected peak value.

$$Th_1 = 0.5 Peak_{previous} \tag{17}$$

For any value greater than $Th_1$, the maximum value of recorded samples of the ECG signal within the search window is chosen as a temporal peak value. Detection is deemed complete when the filtered and processed ECG signal is downward sloping with an amplitude value of less than 10% of the value given to the first adaptive threshold value $Th_1$. The second adaptive threshold value $Th_2$ is given in equation 18.

$$Th_2 = 0.1 Th_1 \tag{18}$$

In order to avoid detecting any false R peaks, every two consecutive peaks should be separated by an interval equal to the $RR_{interval}$, which is updated with each cardiac cycle.

The peak that is to be identified as the actual R peak is located by searching back through the delays introduced throughout the processing steps beginning with the sample in which the first peak was located. Once the actual R peak is located, backward and forward searches through samples of the processed ECG signal are performed to locate the Q onset and the Q offset.

Section 4.4 T Wave and P Wave Delineation

The T wave delineation block 42 and the P wave delineation block 44 are executed in the time domain and are based on adaptive search windows along with adaptive threshold levels to accurately distinguish a T wave peak and a P wave peak from noise peaks. The T wave delineation block 42 and the P wave delineation block 44 are also used to identify different waveform morphologies. Similar to the extended CLT method, boundaries of the search windows are set to be adaptive and relative to the position of the QRS complex location and the RR interval.

Figure 10:
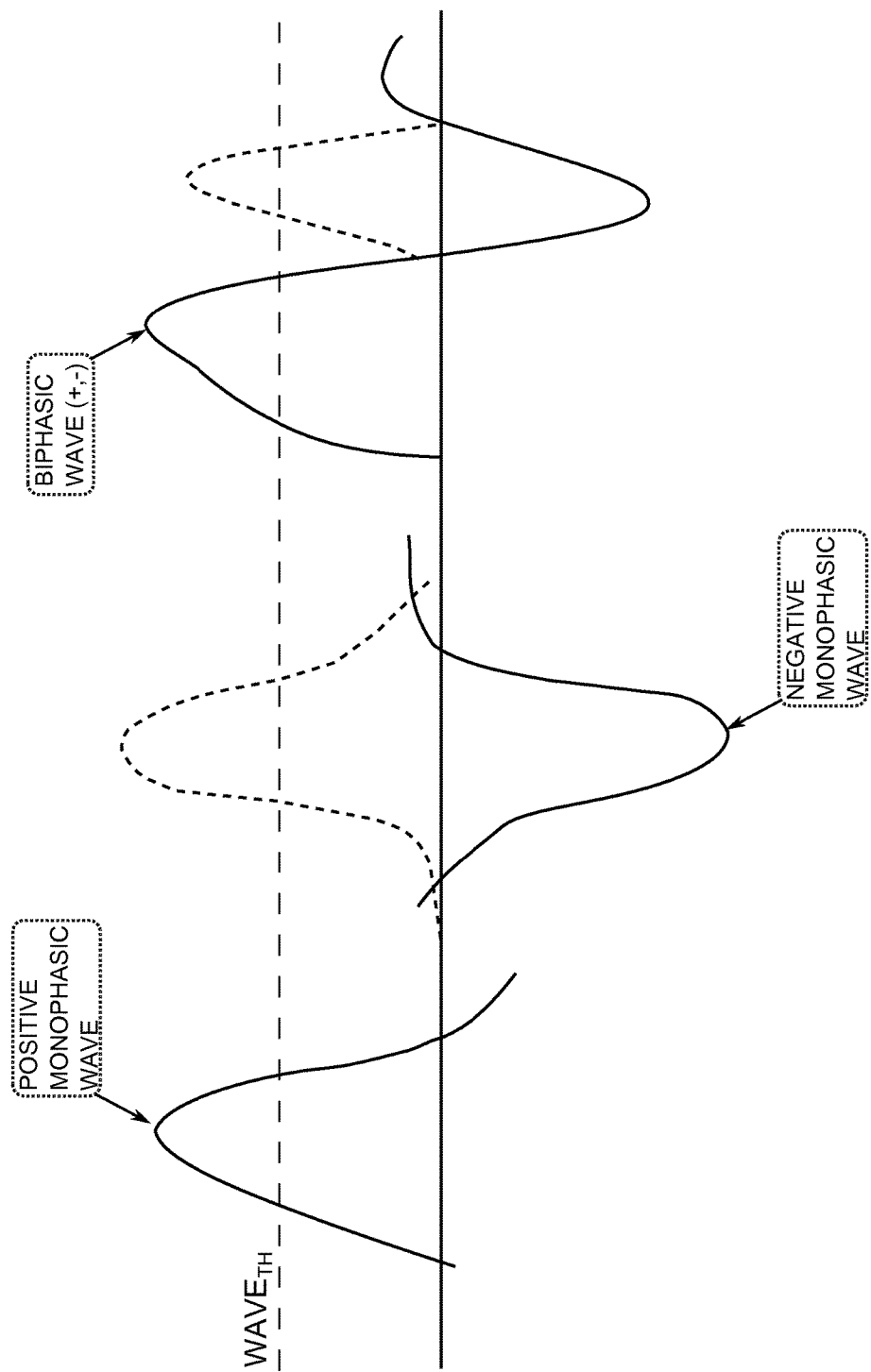
FIG. 10 depicts a generic wave threshold $WAVE_{TH}$ that intersects a positive monophasic wave, a negative monophasic wave, and a biphasic wave (+/−).

In the case of either a T wave or a P wave, a peak position is registered by finding either the local maximum and/or the local minimum within the search window and then comparing the peak's amplitude against an amplitude threshold. FIG. 10 depicts a generic wave threshold $WAVE_{TH}$ that intersects a positive monophasic wave, a negative monophasic wave, and a biphasic wave (+/−). Waves depicted in dashed line in FIG. 10 are reflected onto $WAVE_{TH}$ to show that $WAVE_{TH}$ is also applied to negative monophasic, and negative portions of biphasic waves.

The specific amplitude threshold level $T_{wave_{th}}$ for the T wave is given in equation 19 and the specific amplitude threshold level $P_{wave_{th}}$ for the P wave is given in equation 20.

$$T_{wave_{th}} = \frac{T_{peak}}{R_{peak}} \times t_{thresh_{in}} \tag{19}$$

$$P_{wave_{th}} = \frac{P_{peak}}{R_{peak}} \times p_{thresh_{in}} \tag{20}$$

If a maximum point within the search window exceeds the amplitude threshold level $T_{wave_{th}}$ for the T wave or the amplitude threshold level $P_{wave_{th}}$ for the P wave and a minimum point with in the search window does not, the particular wave located is recognized as a positive monophasic wave and the maximum point is registered as a peak. For a negative monophasic wave, the opposite is true. In case of a biphasic wave, both the local maximum and the absolute value of the local minimum should exceed the threshold in question.

The T wave delineation block 42 (FIG. 1) and the P wave delineation block 44 (FIG. 1) trace onset and offset values, respectively, by finding a sample point corresponding to a zero slope of the filtered ECG signal. The sample point which has zero slope and is located before the peak is identified as an onset point. Similarly, the offset point is located after the peak. At times, however, a derivative sign change occurs that signifies a false detection. To solve this issue, the T wave delineation block 42 and the P wave delineation block 44 each add another criterion to correctly delineate wave boundaries based upon a fact that fiducial points merge smoothly with the isoelectric line. The isoelectric line is approximated as an average value of a heartbeat signature after removing the QRS complex sample points. This action combined with the zero slope location method provides accurate and reliable delineation of a T fiducial point and a P fiducial point.

Section 5. Performance and Results

Section 5.1. ECG Database

In order to evaluate performance of the disclosed blocks, ECG signals from the PhysioNet QT database were used. The PhysioNet QT database contains at least 105 two lead ECG signal recordings that were sampled at 250 HZ. The PhysioNet QT database was accumulated from other databases such as the Massachusetts Institute of Technology-Beth Israel Hospital (MIT-BIH) arrhythmia database, the MIT-BIH ST change database, and the MIT-BIH supraventricular arrhythmia database. A total of 3000 heartbeat signatures captured from a single lead was used to assess the delineation and detection performance of the medical device 10 (FIG. 1) that automatically implements the novel methods of the present disclosure.

Section 5.2. Performance Criteria

Performance of the delineation and detection blocks was measured using metrics such as sensitivity (Se), positive predictability (P⁺), mean error ($\mu$), and standard deviation ($\sigma$). The sensitivity and positive predictability measure the accuracy of the obtained results, where TP represents the quantity of truly detected heartbeat signatures and FN represents the quantity of false detections in which a heartbeat signature exists but is not detected. A false positive variable represented by FP refers to the quantity of invalid detections of a heartbeat signature when none are actually present within the search window. Sensitivity (Se) and positive predictability (P⁺) are given by equations 21 and 22, respectively.

$$Se = \frac{TP}{TP+FN} \times 100 \quad (21)$$

$$P^+ = \frac{TP}{TP+FP} \times 100 \quad (22)$$

Section 5.3. QRS Complex Detection and Delineation

The detection performance for locating fiducial points of the QRS complex obtained by the adaptive thresholding block 30 and the PAT block 32 was compared to related art methods for locating fiducial points of the QRS complex. Table I below lists results of the comparison.

TABLE I

SENSITIVITY AND POSITIVE PREDICTIVITY OF QRS COMPLEX DETECTORS

| Technique | Se | P⁺ |
| --- | --- | --- |
| DWT | 98.66% | 99.64% |
| Extended CLT | 98.59% | 97.86% |
| PAT | 99.83% | 98.65% |
| [4] | 99.69% | 99.77% |
| [6] | 99.92% | 99.88% |
| [7] | 99.63% | 99.89% |
| [24] | 99.24% | 99.88% |

Related art technique [4] is provided in P. S. Hamilton and W. J. Tompkins, "Quantitative Investigation of QRS Detection Rules using MIT/BIH Arrhythmia Database," *Biomedical Engineering, IEEE Transactions on*, no. 12, pp. 1157-1165, 1986. Related art technique [6] is provided by J P Martinez et al., "A wavelet-based ECG delineator: Evaluation on standard databases," *Biomedical Engineering, IEEE Transactions on*, pp. 570-581, 2004. Related art technique [7] is provided in M-W Phyu et al., "A real-time ECG QRS detection ASIC based on wavelet multiscale analysis," in *Solid-State Circuits Conference, IEEE Asian*. IEEE, 2009, pp, 293-296. Related art technique [24] is provided in D. A. Coast and G. G. Cano, "QRS detection based on hidden Markov modeling," in *Engineering in Medicine and Biology Society*, 1989. Images of the Twenty-First Century, *Proceedings of the Annual International Conference of the IEEE Engineering in IEEE*, 1989, pp. 34-35.

The overall sensitivity of the adaptive thresholding block 30 and PAT block 32 for DWT, extended-CLT, and PAT is found at levels of 98.66%, 98.56%, and 99.83%, respectively. Following the same order, the adaptive thresholding block 30 and PAT block 32 achieved a positive predictivity at levels of 99.64%, 97.86%, and 98.65% for all tested heartbeat signatures.

Table II below lists statistical results of the mean and standard deviation for ECG fiducial points by DWT only, extended CLT, and PAT only in comparison with the following related art publications including related art [6] listed above.

TABLE II

QRS COMPLEX DETECTION PERFORMANCE: MEAN AND STANDARD DEVIATION VALUES IN (MS)

| Method | Parameter | $Q_{on}$ | $R_{peak}$ | $Q_{off}$ |
| --- | --- | --- | --- | --- |
| DWT | $\mu$ ms | −3.9915 | −2.5067 | −2.3066 |
|  | $\sigma$ ms | 32.6856 | 17.4503 | 32.6856 |
| Extended CLT | $\mu$ ms | 0.4271 | −3.1248 | 1.9198 |
|  | $\sigma$ ms | 20.1286 | 23.6960 | 31.3776 |
| PAT | $\mu$ ms | −1.5829 | −3.0018 | −2.4964 |
|  | $\sigma$ ms | 27.2937 | 20.3163 | 27.2937 |
| [6] | $\mu$ ms | 4.6 | NA | 0.8 |
|  | $\sigma$ ms | 7.7 | NA | 8.7 |
| [8] | $\mu$ ms | 3.7 | 3.8 | 12.1 |
|  | $\sigma$ ms | 7.8 | 9.8 | 16.6 |
| [23] | $\mu$ ms | 4.1 | −5.2 | 5.1 |
|  | $\sigma$ ms | 8.7 | 15.6 | 12.4 |
| [31] | $\mu$ ms | 9.1 | NA | 2.6 |
|  | $\sigma$ ms | 7.6 | NA | 10.2 |
| [32] | $\mu$ ms | 3.5 | NA | 2.4 |
|  | $\sigma$ ms | 6.1 | NA | 10.3 |

Related art technique [8] is provided by E. B. Mazomenos et al., "A Low-Complexity ECG Feature Extraction Algorithm for Mobile Healthcare Applications," IEEE Journal of Biomedical and Health Informatics, Vol. 17, No. 2, pp. 459-469, 2013. Related art technique [23] is provided by E. B. Mazomenos, et al., "A Time-Domain Morphology and Gradient Based Algorithm for ECG Feature Extraction," in *Industrial Technology (ICIT)*, 2012 IEEE International Conference on IEEE, pp. 117-122, 2012. Related art technique [31] is provided by R. V. Andreao et al., "ECG signal analysis through hidden Markov models," *Biomedical Engineering, IEEE Transactions on*, Vol. 53, No. 8, pp. 1541-1549, 2006. Related art technique [32] is provided by Y. Sun, K. L. Chan, and S. M. Krishnan, "Characteristic wave detection in ECG signal using morphological transform, *"BMC cardiovascular disorders*, Vol. 5, No. 1, pp. 28, 2005. The novel extended CLT method executed by the adaptive thresholding block 30 delineates $Q_{on}$, $R_{peak}$, and $Q_{off}$ with a mean square error of 0.43 ms, −3.12 ms, and 1.92 ms, respectively, are the most accurate delineation results compared to all of the methods listed in Table II. Moreover, the novel self-adaptation of DWT and PAT provide improved accuracy over time in comparison with the other detection and delineation techniques listed in Table II. For example, DWT and PAT both delineate $R_{peak}$ with less mean square error than either the delineation results of related art delineation technique [8] or related art delineation technique [23]. DWT provides more accuracy for $Q_{on}$ delineation in comparison to the related art delineation techniques of [6], [23], and [31]. PAT provides more accuracy for $Q_{on}$ delineation than all of the related art techniques listed in Table II. Similarly, DWT and PAT both provide better $Q_{off}$ accuracy than the related art delineation techniques with the exception of related art delineation technique [6].

Section 5.4 T Wave and P Wave Delineation

Table III below lists mean and standard deviation values for T wave and P wave detection performance. Related art delineation technique [25] listed below is provided by C. Lin, C. Mailhes, and J.-Y. Tourneret, "P- and t-wave delineation in ecg signals using a Bayesian approach and a partially collapsed gibbs sampler." *IEEE Trans. Biomed. Engineering*, Vol. 57, No. 12, pp. 2840-2849, 2010. Related art delineation technique [34] listed below is provided by P. Laguna, R. G. Mark, A. Goldberg, and G. B. Moody, "A Database for Evaluation of Algorithms for Measurement of QT and Other Waveform Intervals in the ECG," in Computers in Cardiology. IEEE, 1997, pp. 673-676.

TABLE III

T AND P WAVE DETECTION PERFORMANCE: MEAN AND STANDARD DEVIATION VALUES IN (Ms)

| Method | Parameter | $T_{peak}$ | $T_{off}$ | $P_{peak}$ | $P_{off}$ |
|---|---|---|---|---|---|
| DWT | μ ms | 2.4564 | 4.1926 | −3.5066 | 2.8188 |
|  | σ ms | 35.2310 | 40.9700 | 28.7175 | 29.5132 |
| Extended CLT | μ ms | −0.7293 | −1.8763 | −2.6958 | 2.5540 |
|  | σ ms | 51.6720 | 58.4000 | 41.4140 | 54.0118 |
| Thresholding | μ ms | −1.0805 | 1.5797 | 2.2328 | −2.8955 |
|  | σ ms | 48.7051 | 56.9635 | 34.5359 | 33.0065 |
| [6] | μ ms | 0.2 | −1.6 | 3.6 | 1.9 |
|  | σ ms | 13.9 | 18.1 | 13.2 | 12.8 |
| [8] | μ ms | 5 | 3.1 | −15.3 | −16.6 |
|  | σ ms | 9.5 | 16 | 29.3 | 20.8 |
| [23] | μ ms | 7.6 | 11.2 | 2.8 | 5.6 |
|  | σ ms | 15 | 20.8 | 25.3 | 28.6 |
| [25] | μ ms | 1.3 | 4.3 | 4.1 | −3.1 |
|  | σ ms | 10.5 | 20.8 | 8.6 | 15.1 |
| [31] | μ ms | NA | 12.1 | NA | −6.1 |
|  | σ ms | NA | 21.5 | NA | 11.7 |
| [32] | μ ms | NA | 8.3 | NA | 12.8 |
|  | σ ms | NA | 12.4 | NA | 13.2 |
| [34] | μ ms | −7.2 | 13.5 | 4.8 | −0.1 |
|  | σ ms | 14.3 | 27 | 10.6 | 12.3 |

As displayed in Table III above, the extended CLT method has the highest detection accuracy for $T_{peak}$, $T_{off}$, $P_{peak}$, and $P_{off}$ of all listed detection methods with the exception of related art technique [6]. In addition, DWT, extended CLT, and thresholding provide the highest accuracy in delineating $T_{off}$ in terms of mean square error compared with [25], [31], [34], and [23]. Moreover, DWT, extended CLT, and thresholding provide higher accuracy for delineating $P_{peak}$ in terms of mean square error than the related art delineation method of [8]. The delineation of $T_{peak}$ by extended CLT and thresholding within the time domain provides the highest accuracy in terms of mean square error in comparison with [8], [23], [25], and [34], whereas DWT lies in between. On the other hand, the least mean square error for delineating $P_{off}$ is improved in [6] and [34] compared to the self-adaptive methods of DWT, extended CLT and thresholding, yet these self-adaptive methods are more accurate in terms of least mean square error in comparison with [8], [23], [25], [31], and [32].

Section 5.5. Representative Results

Figure 11:
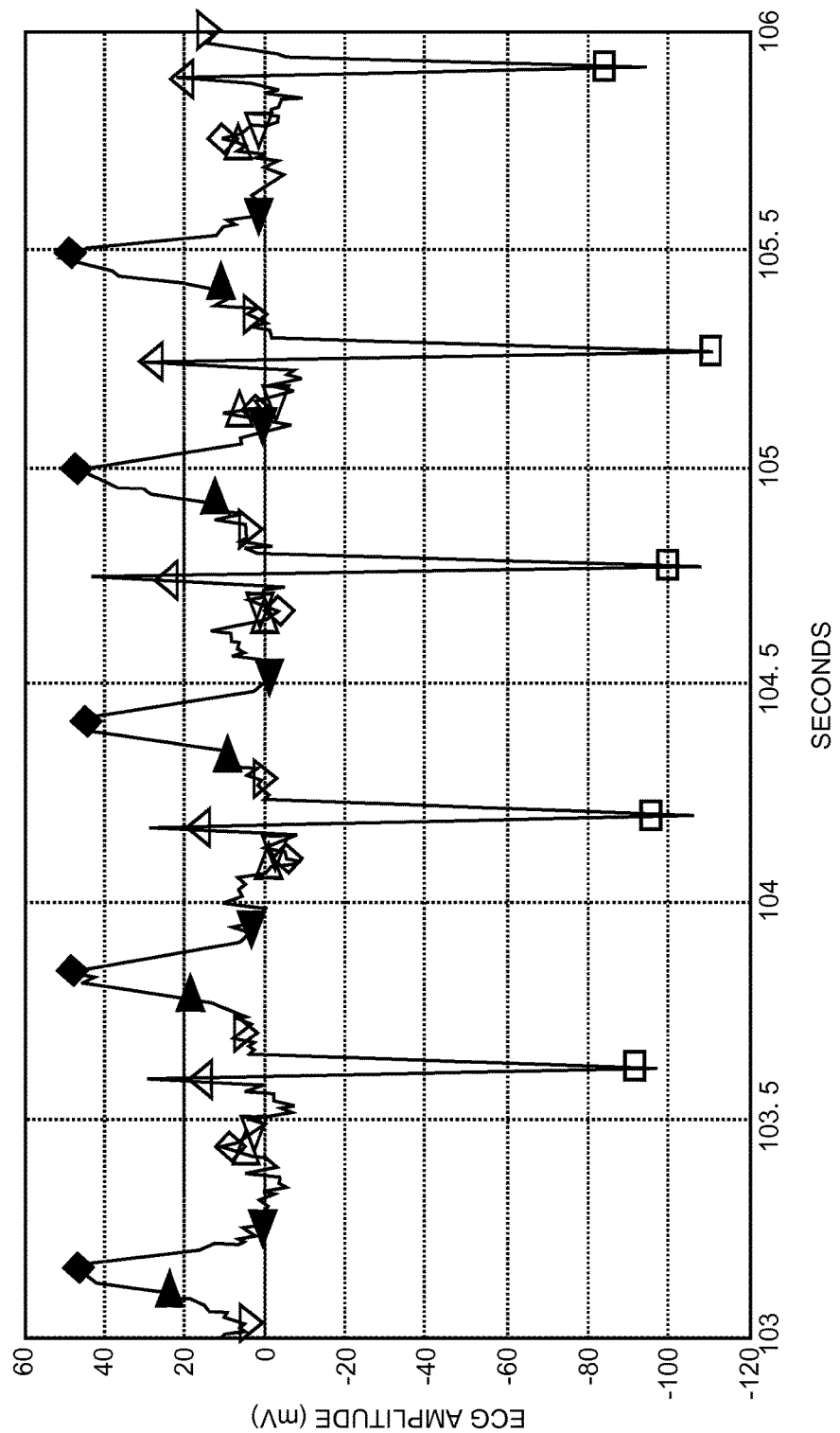
FIG. 11 is an ECG graph with marked fiducials located using DWT.
Figure 12:
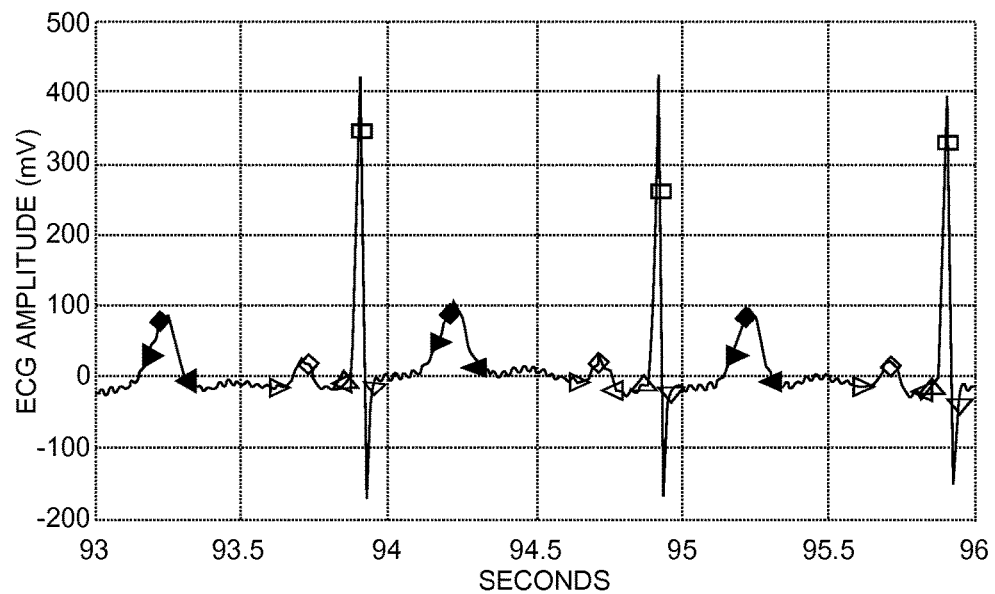
FIG. 12 is an ECG graph with marked fiducials located using extended CLT.
Figure 13:
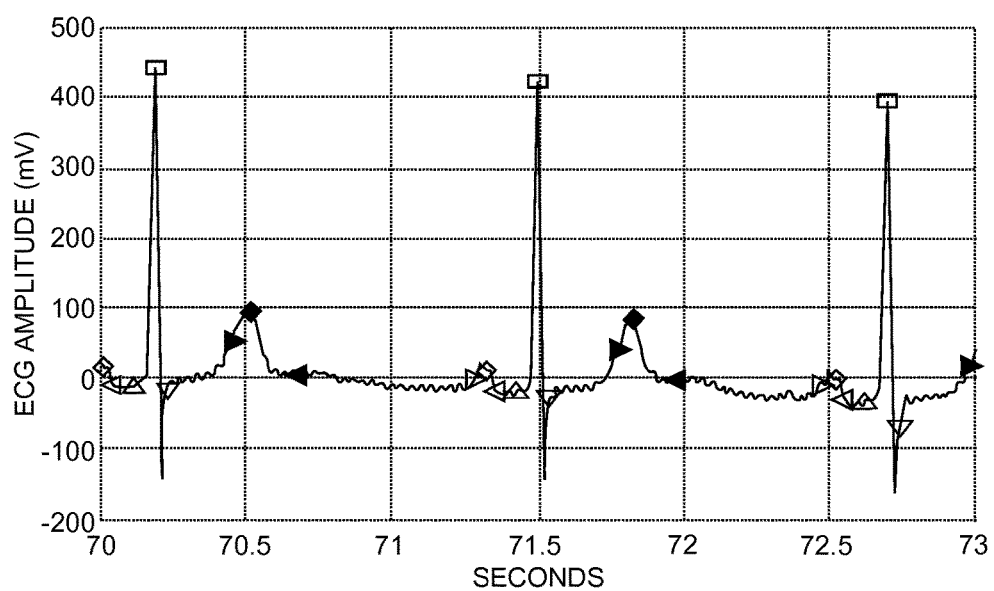
FIG. 13 is an ECG graph with marked fiducials located using thresholding in the time domain.
Figures 17A, 17B:
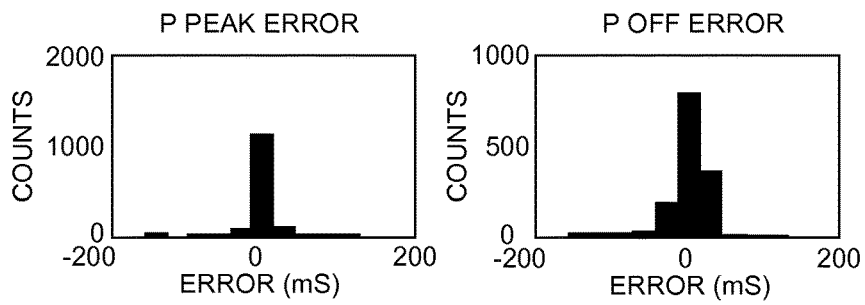
FIG. 17A is an error distribution bar graph for P peak error using DWT only.
FIG. 17B is an error distribution bar graph for P off error using DWT only.
Figures 17C, 17D:
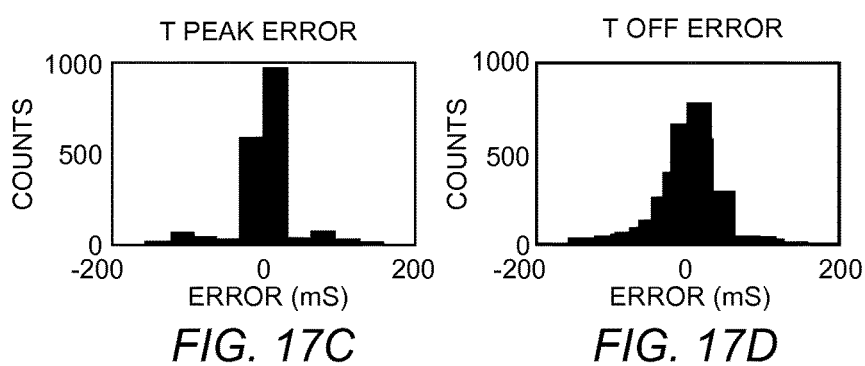
FIG. 17C is an error distribution bar graph for T peak error using DWT only.
FIG. 17D is an error distribution bar graph for T off error using DWT only.
Figures 18A, 18B:
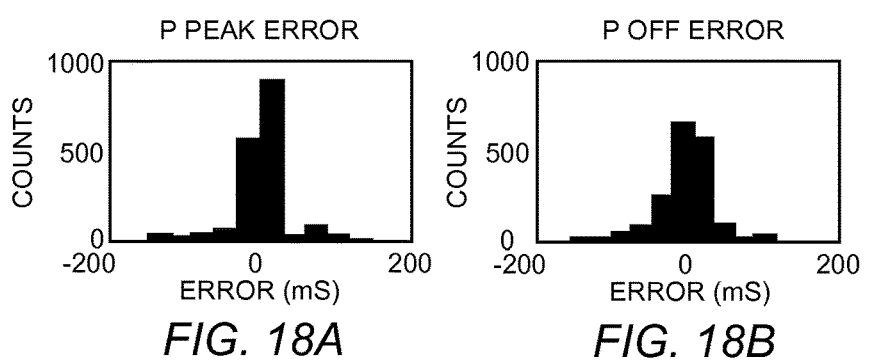
FIG. 18A is an error distribution bar graph for P peak error using extended CLT.
FIG. 18B is an error distribution bar graph for P off error using extended CLT.
Figures 18C, 18D:
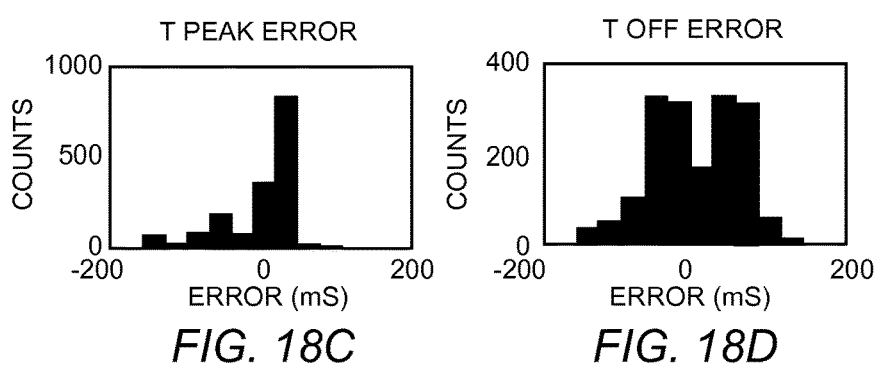
FIG. 18C is an error distribution bar graph for T peak error using extended CLT.
FIG. 18D is an error distribution bar graph for T off error using extended CLT.
Figure 19A:
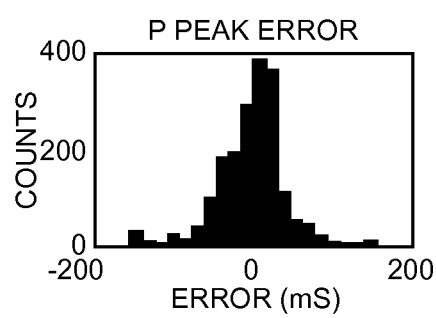
FIG. 19A is an error distribution bar graph for P peak error using thresholding in the time domain.
Figure 19B:
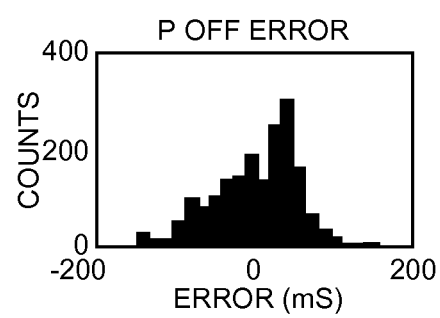
FIG. 19B is an error distribution bar graph for P off error using thresholding in the time domain.
Figure 19C:
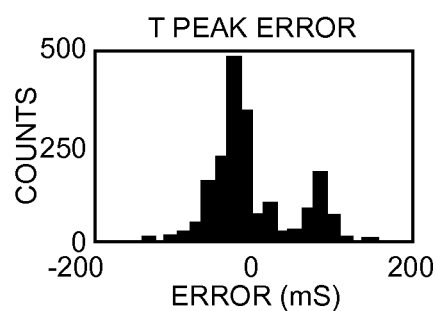
FIG. 19C is an error distribution bar graph for T peak error using thresholding in the time domain.
Figure 19D:
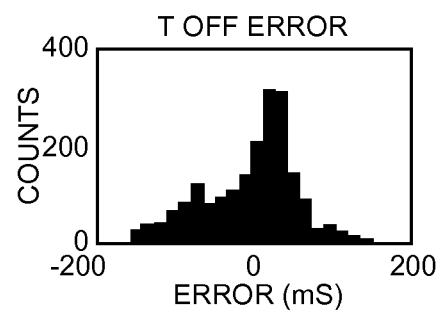
FIG. 19D is an error distribution bar graph for T off error using thresholding in the time domain.

The delineation results of an ECG waveform obtained by DWT, extended CLT, and time domain thresholding are shown in FIGS. 11, 12, and 13, respectively, for different waveform morphologies with marked fiducial points for $P_{peak}$, $P_{off}$, $Q_{on}$, $R_{peak}$, $Q_{off}$, $T_{peak}$, and $T_{off}$. The error distribution for each extracted ECG fiducial point based on the QT database (QTDB) experimentation is illustrated in FIGS. 14A through 14C, 15A through 15C, 16A through 16C, 17A through 17D, 18A through 18D and 19A through 19D. The self-adaptive methods of DWT, extended CLT and thresholding in the time domain have a Gaussian distribution for most of the fiducial point errors with means centered about zero.

Section 6. Conclusion

This disclosure provides self-adaptive ECG processing to detection and delineation type medical devices based on DWT, thresholding in the time domain, and extended CLT. Extended CLT provided herein is a novel method that benefits from both CLT and DWT through combined real-time implementation. One benefit provided by DWT is T wave and P wave detection and delineation with different waveform morphologies. On the other hand, the presently disclosed thresholding in the time domain provided by the adaptive thresholding block 30 is self-adaptive and based upon ECG signal amplitude without the need for any type of transformation.

Extended CLT, DWT, and thresholding in the time domain each include adaptive search windows and thresholds that adjusted in range for each heartbeat signature in order to locate positions of the QRS complex, T wave, and P wave. Depending on continuously updated estimates of peak amplitudes and the RR interval, values for threshold levels and boundaries for the adaptive search windows are adjusted. These actions allow for tracking changes in upcoming sections of the ECG signal. For example, a decrease in the RR interval will signify an increase in heartbeat rate. As such, the adaptive search windows are adjusted to take into account changes in heart beat rate. The self-adaptive nature of extended CLT, DWT, and thresholding in the time domain via automated ECG processing by a medical device has substantially improved the accuracy of locating the QRS complex, along with finding accurate locations of the T wave and the P wave within an ECG signal. Further still, the novelty of the extended CLT provided by the present disclosure has the least mean square error in comparison to related art delineation techniques.

Those skilled in the art will recognize improvements and modifications to the embodiments of the present disclosure. All such improvements and modifications are considered within the scope of the concepts disclosed herein and the claims that follow.

What is claimed is:

1. A method for a medical device having automated electrocardiogram (ECG) feature extraction comprising:
    receiving by way of input circuitry an ECG signal generated by heartbeats;
    processing the ECG signal by substantially simultaneously performing in parallel both a discrete wavelet transform (DWT) process that generates DWT data associated with a T wave and a P wave of the ECG signal and a curve length transform (CLT) process that generates CLT data associated with a QRS complex of the ECG signal by way of processing circuitry coupled to the input circuitry;
    detecting an R peak of the QRS complex from the CLT data by identifying an amplitude within the CLT data that is greater than a QRS threshold updated as a portion of a sum of a previous QRS threshold associated with a previous one of the heartbeats and an average of CLT data generated from the previous one of the heartbeats; and
    detecting a T wave peak and a P wave peak of the ECG signal from the DWT data by identifying within a forward search window following the QRS complex an amplitude that is greater than a T threshold updated as an average of the ECG signal within the forward search window and by identifying within a backward search window before the QRS complex an amplitude that is greater than a P threshold updated as an average of the ECG signal within the backward search window.

2. The method for the medical device having automated ECG feature extraction of claim 1 further including adjusting locations of boundaries of the forward search window and the backward search window relative to the QRS complex and an RR interval associated with the previous heartbeat.

3. The method for the medical device having automated ECG feature extraction of claim 1 further including extracting parameters that include PQ interval variability, QP interval variability, RT interval variability, TR interval variability, PS interval variability, and SP interval variability automatically by way of feature extraction circuitry coupled to the processing circuitry.

4. The method for the medical device having automated ECG feature extraction of claim 1 further including filtering the ECG signal by way of the input circuitry to substantially reduce noise having frequencies lower and higher than at least one wave within the ECG signal that includes the QRS complex.

5. A medical device having automated electrocardiogram (ECG) feature extraction comprising:
    input circuitry configured to receive an ECG signal generated from heartbeats; and
    processing circuitry configured to:
        execute a curve length transform (CLT) that generates CLT data associated with a QRS complex of the ECG signal;
        execute a discrete wavelet transform (DWT) that generates DWT data associated with a T wave and a P wave of the ECG signal, wherein the CLT and DWT are executed in parallel at substantially the same time;
        detect an R peak of the QRS complex from the CLT data by identifying an amplitude within the CLT data that is greater than a QRS threshold updated as a portion of a sum of a previous QRS threshold associated with a previous one of the heartbeats and an average of CLT data generated from the previous one of the heartbeats; and
        detect a T wave peak and a P wave peak of the ECG signal from the DWT data by identifying within a forward search window following the QRS complex an amplitude that is greater than a T threshold updated as an average of the ECG signal within the forward search window and by identifying within a backward search window before the QRS complex an amplitude that is greater than a P threshold updated as an average of the ECG signal within the backward search window.

6. The medical device having automated ECG feature extraction of claim 5 wherein the processing circuitry is further configured to adjust locations of boundaries of the forward search window and the backward search window relative to the QRS complex and an RR interval associated with the previous heartbeat.

7. The medical device having automated ECG feature extraction of claim 5 further including feature extraction circuitry coupled to the processing circuitry to extract parameters that include PQ interval variability, QP interval variability, RT interval variability, TR interval variability, PS interval variability, and SP interval variability.

8. The medical device having automated ECG feature extraction of claim 7 further including machine learning circuitry coupled to the feature extraction circuitry and configured to decide if a ventricular arrhythmia event is occurring based upon parameters extracted from the ECG signal.

9. The medical device having automated ECG feature extraction of claim 5 wherein the input circuitry is configured to provided band-pass filtering to substantially reduce noise having frequencies lower and higher than at least one wave within the ECG signal that includes the QRS complex.

10. The medical device having automated ECG feature extraction of claim 5 wherein the input circuitry includes a low pass filter to reduce low frequency noise from within the ECG signal.

11. The medical device having automated ECG feature extraction of claim 5 wherein the input circuitry includes a high pass filter to reduce high frequency noise from within the ECG signal.

* * * * *